US006395351B1

(12) United States Patent
Benecke et al.

(10) Patent No.: US 6,395,351 B1
(45) Date of Patent: May 28, 2002

(54) POLYMERISABLE LIQUID CRYSTALLINE COMPOUNDS

(75) Inventors: Carsten Benecke, Weil am Rhein (DE); Teodor Lukàc, Basel (CH); Angela Ohlemacker, Wehr (DE)

(73) Assignee: Rolic AG, Zug (CH)

( * ) Notice: Subject to any disclaimer, the term of this patent is extended or adjusted under 35 U.S.C. 154(b) by 0 days.

(21) Appl. No.: 09/443,214

(22) Filed: Nov. 19, 1999

Related U.S. Application Data

(63) Continuation of application No. PCT/IB98/00789, filed on May 22, 1998.

(30) Foreign Application Priority Data

May 22, 1997  (EP) .............................................. 97108259

(51) Int. Cl.$^7$ ........................ C09K 19/42; C09K 19/30; C09K 19/20; C07C 69/92; C07C 69/94
(52) U.S. Cl. .............. 428/1.1; 252/299.63; 252/299.64; 252/299.65; 252/299.66; 252/299.67; 560/64; 560/118; 560/130; 560/144
(58) Field of Search ........................ 252/299.01, 299.61, 252/299.63, 299.64, 299.65, 299.66, 299.67; 428/1.1; 560/64, 118, 130, 144

(56) References Cited

U.S. PATENT DOCUMENTS

| | | |
|---|---|---|
| 4,130,502 A | 12/1978 | Eidenschink et al. |
| 4,237,026 A | 12/1980 | Eidenschink et al. |
| 4,696,990 A | 9/1987 | Noonan et al. |
| 4,770,503 A | 9/1988 | Buchecker et al. |
| 4,871,472 A | 10/1989 | Krauss et al. |
| 5,013,478 A | 5/1991 | Petrzilka |
| 5,043,095 A | 8/1991 | Bahr et al. |
| 5,401,437 A | 3/1995 | Im |
| 5,518,652 A | 5/1996 | Parri et al. |
| 5,567,349 A | 10/1996 | Kelly et al. |
| 5,593,617 A | 1/1997 | Kelly et al. |
| 5,700,393 A | 12/1997 | Kelly |
| 5,707,544 A | 1/1998 | Kelly |
| 5,744,057 A | 4/1998 | Meyer et al. |
| 6,174,457 B1 * | 1/2001 | Kato et al. .............. 252/299.63 |

FOREIGN PATENT DOCUMENTS

| | | |
|---|---|---|
| DE | 4408171 A1 | 9/1995 |
| EP | 0648 827 A1 | 4/1995 |
| EP | 0689 065 A1 | 6/1995 |
| GB | 2155465 A | 9/1985 |
| GB | 2298202 A | 8/1996 |
| WO | WO 93/22397 | 11/1993 |
| WO | WO 95/22586 | 8/1995 |
| WO | 98/13321 * | 4/1998 |

OTHER PUBLICATIONS

Aquilera et a. "Liquid crystalline Main Chain Polymers with Highly Flexible Siloxane Spacers", Makromol. Chem, 184, 253–262, 1983.*

Shibaev V.P. et al: "Novel Atropoisomeric Binaphthaly–Containing Liquid Crystalline Copolymers Forming Chiral Nematic Phases" Liquid Crystals 1997, vol. 22, No. 4 pp. 451–457.

(List continued on next page.)

Primary Examiner—Shean C. Wu
(74) Attorney, Agent, or Firm—Finnegan, Henderson, Farabow, Garrett & Dunner, L.L.P.

(57) ABSTRACT

Compounds with the general formula (I): $R-S^1-A-Z^1-B-S^2-R$, where A and B are independent ring systems with the formulae $(a^1)$, $(a^2)$ or (b),

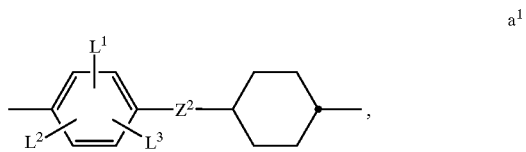

$a^1$

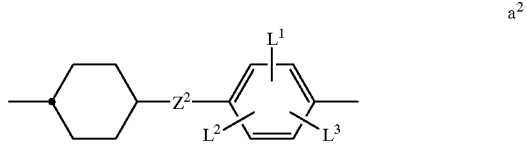

$a^2$

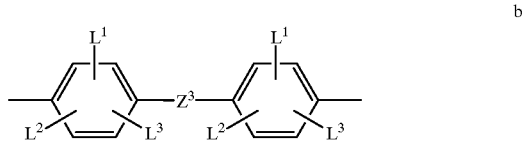

b whereby in the trans-1,4-cyclohexylene ring, one or two non-adjacent $CH_2$ groups may be replaced by oxygen, and whereby, in the 1,4-phenylene ring, one or two non-adjacent CH groups may be replaced by nitrogen; $L^1$, $L^2$, $L^3$ represent, independently, hydrogen, $C_1-C_{20}$-alkyl, $C_1-C_{20}$-alkenyl, $C_1-C_{20}$-alkyloxy, $C_1-C_{20}$-alkyloxy carbonyl, formyl, $C_1C_{20}$-alkyl carbonyl, $C_1-C_{20}$-alkyl carbonyloxy, halogen, cyano or nitro; $Z^1$, $Z^2$, $Z^3$ represent, independently, a single bond, $-CH_2CH_2-$, $-CH_2O-$, $-OCH_2-$, $-COO-$, $-OOC-$, $-(CH_2)_4-$, $-O(CH_2)_3-$, $-(CH_2)_3O-$ or $-C\equiv C-$; $S^1$, $S^2$ represent a spacer unit; R represents crosslinkable groups, with the proviso that at least one of the ring systems A or B represents a ring system with the formula $(a^1)$ or $(a^2)$, $Z^1$ or $Z^2$ denoting a single bond.

20 Claims, No Drawings

OTHER PUBLICATIONS

Kelly S.M: "The Synthesis and Liquid Crystal Transition Temperatures of Some Weakly Polar Nematic Trans–4–Substituted–Cyclohexyl (E)–Alk–2–Enoates" Liquid Crystals 1994, vol. 17, No. 2, pp. 211–225.

Wilds A L et al. Steroid Analogs Lacking Ring C. III. Synthesis Of 4–(trans–4[1] —Hydroxycyclohexyl–Cyclohexanone[1], J. Am. Chem. Soc. vol. 76, No. 7, 1954 pp 1733–1736.

Derwent Abstract of DE 4408171, 1995.

Derwent Abstract of EP 0689065, 1996.

Derwent Abstract of WO 95/22586, 1995.

* cited by examiner

POLYMERISABLE LIQUID CRYSTALLINE COMPOUNDS

This application is a continuation of International Application No. PCT/IB98/00789, filed May 22, 1998, the content of which is incorporated herein by reference.

This invention relates to new photo-crosslinkable liquid crystalline compounds, liquid crystalline mixtures which contain such compounds, and their use in the cross-linked condition as optical components.

Photo cross-linkable liquid crystals, which are provided with an appropriate amount of a photoinitiator, can be oriented on a substrate or in a cell by suitable orienting layers or in a field and then in this state can be cross-linked by irradiation with light of a suitable wavelength. The liquid crystal orientation in the structure thus produced is maintained, even at high temperatures. Optical components, such as waveguides, optical grids, filters and retarders, piezoelectric cells and cells with non-linear optical (NLO) properties etc. may therefore be produced using this procedure. Such optical elements may be used, for example, for frequency doubling (SHG) or in colour filters.

The optical properties of the liquid crystal materials used in the manufacture of the aforementioned optical components such as birefringence, refractive indices, transparency, etc. are selected according to the field of application in which they are to be used. Thus materials for optical filters, for example, must exhibit a high birefringence Δn at low dispersion n=f(λ).

In addition to the use of photo-crosslinkable liquid crystals in the manufacture of optical components, such liquid crystalline materials are also suitable as glass fibre cladding for optical data transmission. Photo-crosslinkable liquid crystals exhibit anisotropic thermal conductivity, enabling heat to flow in certain directions. The use of such materials reduces the thermal coefficients of expansion and reduces microdistortion losses. This results in increased mechanical stability.

Liquid crystal media used in the manufacture of optical components are generally used in the form of liquid crystal mixtures. It is desirable that liquid crystal components are chemically and thermally stable, readily soluble in conventional solvents, and stable to electrical fields and electromagnetic radiation. They should have a suitable mesophase in the temperature range of from approx. 25° to approx. +100° C., particularly from approx. 25° C. to approx. +80° C. Moreover, since liquid crystals are usually used as mixtures of several components, it is important for the components to be well miscible with one another.

Conventional photochemically oligomerisable or polymerisable liquid crystals generally have a high melting and clearing point. The disadvantage of this is that spontaneous, thermal polymerisation may occur prematurely during processing, this polymerisation occurring at temperatures just below the clearing point where the viscosity is low and therefore favourable for a good orientability. This spontaneous polymerisation represents a significant problem as it results in the formation of domains, which substantially impairs the optical and thermal properties in the crosslinked layers produced. In an attempt to overcome this problem, complicated liquid crystal mixtures having several components have been used. Although the lower melting and clarifying points of these mixtures means that they can be processed at lower temperatures it presents the risk of crystallisation of the liquid crystal components.

There is, therefore, a need for photochemically oligomerisable or polymerisable compounds exhibiting relatively lower melting and higher clearing points. Such compounds can be satisfactorily processed in the liquid crystalline condition at temperatures above room temperature, and also in solution. These compounds find particular application in the manufacture of optical components. There is also a need for compounds that can be readily orientated and structured without the formation of domains, and which also exhibit excellent thermal and long-term stability in the crosslinked condition. There is also a need for liquid crystal mixtures with an adjustable optical anisotropy. Liquid crystal mixtures having an adjustable anisotropy are considered to be particularly suitable for the manufacture of optical retarders, for example, in which the optical retardation may be adjusted.

Conventional photochemically oligomerisable or polymerisable liquid crystals, such as those described in EP-A-0 331 233, ACS Symp. Ser. (1996)), 632, 182–189 and in Chem. Mater. (1996), 8 (10), 2451–2460, for example, consist mainly of aromatic rings, and therefore generally exhibit a very high optical anisotropy.

The present invention seeks to address at least some of these problems. A first aspect of the present invention provides compounds with the general formula I:

$$R-S^1-A-Z^1-B-S^2-R \qquad I$$

where

A and B are independent ring systems with the formulae $a^1$, $a^2$ or b,

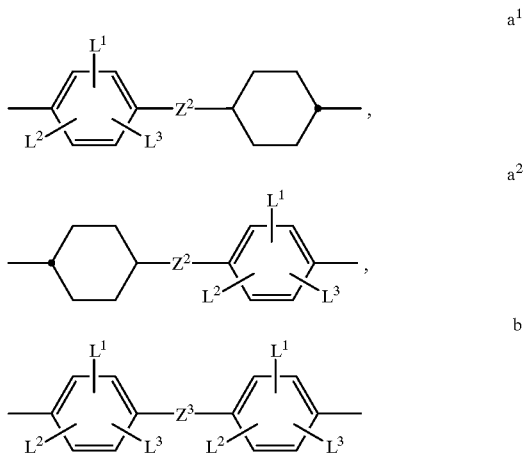

wherein, in teh trans-1,4-cyclohexylene ring, one or two non-adjacent $CH_2$ groups may be replaced by oxygen, and whereby, in the 1,4-phenylene ring, one or two non-adjacent CH groups may be replaced by nitrogen;

$L^1$, $L^2$, $L^3$ represent, independently, hydrogen, $C_1$–$C_{20}$-alkyl, $C_1$–$C_{20}$-alkenyl, $C_1$–$C_{20}$-alkoxy, $C_1$–$C_{20}$-alkyoxycarbonyl, formyl, $C_1$–$C_{20}$-alkylcarbonyl, $C_1$–$C_{20}$-alkylcarbonyloxy, halogen, cyano or nitro;

$Z^1$, $Z^2$, $Z^3$ represent, independently, a single bond, —$CH_2CH_2$—, —$CH_2O$—, —$OCH_2$—, —COO—, —OOC—, —$(CH_2)_4$—, —$O(CH_2)_3$—, —$(CH_2)_3O$— or —C≡C—;

$S^1$, $S^2$ represent, independently, a spacer unit, such as a straight chain or branched alkylene grouping —$(CH_2)_r$—, substituted if necessary singly or multiply with, for example, fluorine, or —$((CH_2)_2—O)_r$—, or a chain with the formula —$(CH_2)_r$—Y—$(CH_2)_s$—, where Y represents a single bond or a linking functional group such as —O—, —COO—, —OOC—, —NR$^1$—, NR$^1$—CO—, —CO—NR$^1$—, —NR$^1$—COO—, —OCO—NR$^1$—, —NR$^1$—CO—NR$^1$—, —O—OC—O—, —CH=CH—, —C≡C—; where R$^1$ represents hydrogen or low alkyl, and where r and s each represent a whole number from 0 to 20 on condition that 2≦(r+s)≦20;

R represents crosslinkable groups with the structure CH$_2$=CH—, CH2=CH—COO—, CH$_2$=C(CH$_3$)—COO—, CH$_2$=C(Cl)—COO—, CH$_2$=C(Ph)—COO—, CH$_2$=CH—COO—Ph—, CH$_2$=CH—CO—NH—, CH$_2$=C(CH$_3$)—CONH—, CH$_2$=C(Cl)—CONH—, CH$_2$=C(Ph)—CONH—, CH$_2$=C(COOR')—CH$_2$—COO—, CH$_2$=CH—O—, CH$_2$=CH—OOC—, Ph—CH=CH—, CH$_3$—C(=NR')—, cis- or trans-HOOC—R'=CR'—COO—,

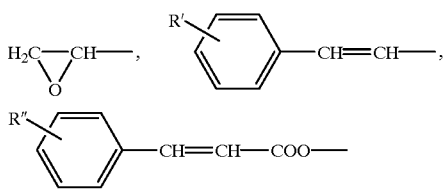

Ph represents a phenyl group,

R' represents methyl, ethyl, propyl, butyl or pentyl;

R" represents methyl, methoxy, cyano or halogen, with the proviso that at least one of the ring systems A or B represents a ring system with the formula a$^1$ or a$^2$, Z$^1$ and/or Z$^2$ represents a single bond, and —R—S$^1$ and R—S$^2$ do not contain —O—O— or —N—O— groups.

Compounds containing a structural unit with the formulae a$^1$ or a$^2$ in the molecule

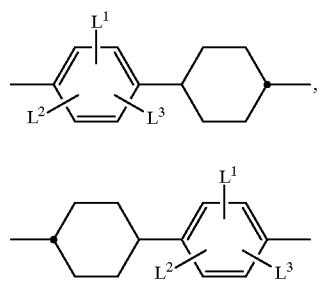

(that is to say, a structural unit with the above-mentioned formulae a$^1$ and a$^2$ and in which Z$^2$ represents a single bond)

have been found to exhibit relatively high clearing points and can be processed at room temperature, preferably as components of liquid crystal mixtures. It is also possible to orientate and structure the compounds or mixtures thereof without the formation of domains. As a component of a LC mixture, they are able to improve the orientability of the liquid crystal mixture on orientation layers thereby improving the contrast of optical display devices. In addition they exhibit extremely good thermal and long-term stability.

By the expression $C_1$–$C_{20}$-alkyl, $C_1$–$C_{20}$-alkoxy, $C_1$–$C_{20}$-alkoxycarbonyl, $C_1$–$C_{20}$-alkylcarbonyl, $C_1$–$C_{20}$-alkylcarbonyloxy it should be understood to mean, in the context of this invention, straight or branched chain saturated hydrocarbon residues, with up to 20 carbon atoms, e.g. methyl, ethyl, propyl, butyl, pentyl, hexyl, heptyl, octyl, nonyl, decyl, undecyl, dodecyl, methoxy, ethoxy, n-propoxy, i-propoxy, butoxy, pentyloxy, hexyloxy, heptyloxy, octyloxy, nonyloxy, decyloxy, undecyloxy, dodecyloxy, methoxycarbonyl, ethoxycarbonyl, propoxycarbonyl, butoxycarbonyl, pentyloxycarbonyl, liexyloxycarbonyl, octyloxycarbonyl, nonyloxycarbonyl, decyloxycarbonyl, undecyloxycarbonyl, dodecyloxycarbonyl, methylcarbonyl, ethylcarbonyl, propylcarbonyl, butylcarbonyl, pentylcarbonyl, hexylcarbonyl, octylcarbonyl, nonylcarbonyl, decylcarbonyl, undecylcarbonyl, dodecylcarbonyl, methylcarbonyloxy, ethylcarbonyloxy, propylcarbonyloxy, butylcarbonyloxy, pentylcarbonyloxy, hexylcarbonyloxy, octylcarbonyloxy, nonylcarbonyloxv, decylcarbonyloxy, undecylcarbonyloxy, dodecylcarbonyloxy, and the like. Especially preferred groups have 1 to 12 carbon atoms and are unbranched.

By the expression $C_1$–$C_{20}$-alkenyl it should be understood to mean, in the context of this invention, alkenyl groups with 3 to 20 carbon atoms, such as 2E-alkenyl, 3Z-alkenyl, 4E-alkenyl and alkenyl with a terminal double bond, e.g. alkyl, 3-butenyl, 4-pentenyl, 5-hexenyl, 6-heptenyl, 7-octenyl, 8-nonenyl, 9-decenyl, 10-undecenyl and the like. Especially preferred are alkenyls with a terminal double bond having 3 to 12 carbon atoms.

By the expression halogen it should be understood to mean, in the context of this invention, fluorine, chlorine, bromine, iodine. Compounds containing fluorine and chlorine are particularly preferred.

Preferred compounds with formula I are compounds with formulae I-A to I-F

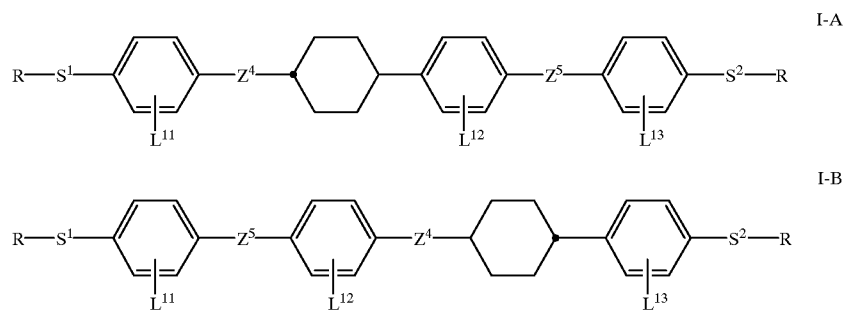

I-C
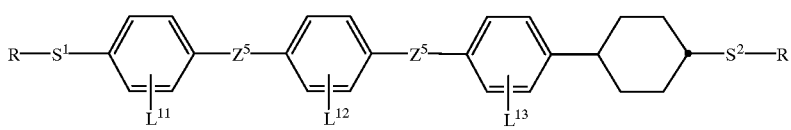

I-D
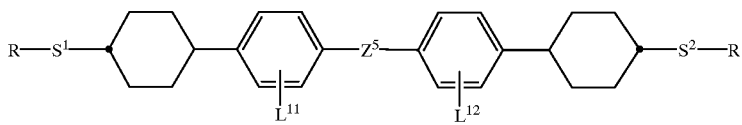

I-E
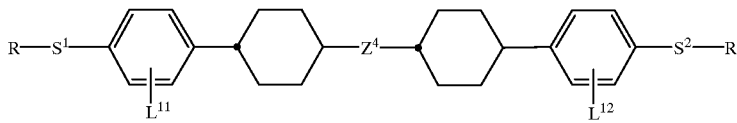

I-F
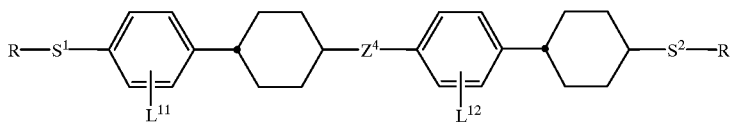

wherein, one or two non-adjacent $CH_2$ groups of the trans-1,4-cyclohexylene ring may be replaced by oxygen and one or two non-adjacent CH groups of the 1,4-phenylene ring, may be replaced by nitrogen;

$L^{11}$, $L^{12}$, $L^{13}$ represent, independently, hydrogen, $C_1$–$C_{20}$-alkykl, $C_1$–$C_{20}$-alkenyl, $C_1$–$C_{20}$-alkoxy, $C_1$–$C_{20}$-alkoxycarbonyl, formyl, $C_1$–$C_{20}$-alkylcarbonyl, $C_1$–$C_{20}$-alkylcarbonyloxy, halogen, cyano or nitro;

$Z^4$ represents a single bond, —$CH_2CH_2$—, —$CH_2O$—, —$OCH_2$—, —COO—, —OOC—, —$(CH_2)_4$—, —$O(CH_2)_3$—, —$(CH_2)_3O$— or C≡C—;

$Z^5$ represents a single bond, —$CH_2CH_2$—, —$CH_2O$—, —$OCH_2$—, —COO—, —OOC—, or —C≡C—; and $S^1$, $S^2$ and R have the meaning indicated in Formula I.

Compounds with the formulae I-A, I-B and I-D are especially preferred.

Of the compounds with formula I-A, particular preference is given to compounds with the formula I-A-1 and I-A-2 alkoxycarbonyl, formyl, $C_1$–$C_{12}$-alkylcarbonyl, $C_1$–$C_{12}$-alkylcarbonyloxy, fluorine, chlorine, cyano or nitro;

$Z^4$ represents —$CH_2CH_2$—, —$OCH_2$, —COO—, —OOC—;

$Z^5$ represents a single bond, —$CH_2CH_2$—, —COO—, —OOC—, or —C≡C—;

R represents a crosslinkable groups with the structure $CH_2$=CH—, $CH_2$=CH—COO—, $CH_2$=C($CH_3$)—COO—, $CH_2$=C(Cl)—COO—,

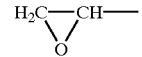

especially $CH_2$=CH—COO—;

m, n each represent, independently, a whole number from 2 to 20, especially from 2 to 12.

Of the compounds with the formula I-B, particular preference is given to compounds with formula I-A-1
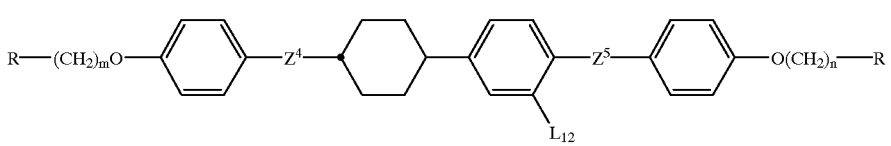

I-A-2
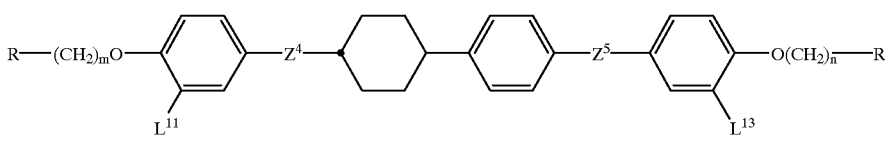

wherein $L^{11}$, $L^{12}$, $L^{13}$ represent, independently, hydrogen, $C_1$–$C_{12}$-alkykl, $C_1$–$C_{12}$-alkenyl, $C_1$–$C_{12}$-alkoxy, $C_1$–$C_{12}$-

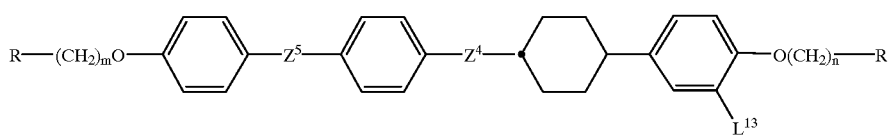

IB-1 wherein
- $L^{13}$ represents hydrogen, $C_1$–$C_{12}$-alkykl, $C_1$–$C_{12}$-alkenyl, $C_1$–$C_{12}$-alkoxy, $C_1$–$C_{12}$-alkoxycarbonyl, formyl, $C_1$–$C_{12}$-alkylcarbonyl, $C_1$–$C_{12}$-alkyl-carbonyloxy, fluorine, chlorine, cyano or nitro;
- $Z^4$ represents —CH$_2$—CH$_2$—, —OCH$_2$—, —COO—, —OOC—; particularly —COO—;
- $Z^5$ represents a single bond, —CH$_2$CH$_2$—, —COO—, —OOC— or —C≡C—; particularly a single bond;
- R represents a crosslinkable group with the structure CH$_2$=CH—, CH$_2$=CH—COO—, CH$_2$=C(CH$_3$)—COO—, CH$_2$=C(Cl)—COO—,

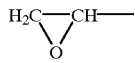

especially CH$_2$=CH—COO—;
- m, n each represent, independently, a whole number from 2 to 20, especially from 2 to 12.

Of the compounds with formula I-D, quite particular preference is given to compounds of formula I-D-1

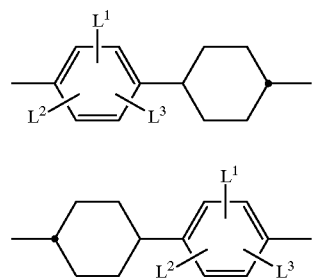

a1′ a2′

Compounds of formula (I) having the structural element $a^1$ or $a^2$ may be prepared from compounds of formula (II), a 4-(trans-4-hydroxycyclohexyl)phenol. The compounds of formula (II) are also new and fall within the scope of the invention.

I-D-1

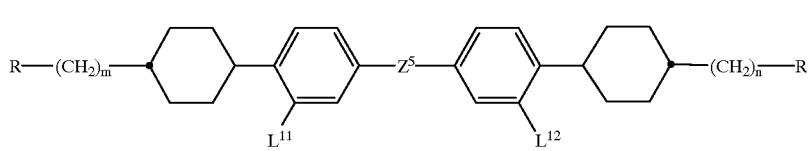

wherein
- $Z^5$ represents a single bond, —CH$_2$CH$_2$—, —COO—, —OOC— or —C≡C—;
- $L^{11}$, $L^{12}$ represent, independently, hydrogen, $C_1$–$C_{12}$-alkyl, $C_1$–$C_{12}$-alkenyl, $C_1$–$C_{12}$-alkoxy, $C_1$–$C_{12}$-alkoxy-carbonyl, formly, $C_1$–$C_{12}$-alkylcarbonyl, $C_1$–$C_{12}$-alkylcarbonyloxy, fluorine, chlorine, cyano or nitro;
- R represents a crosslinkable group with the structure CH$_2$=CH—, CH$_2$=CH—COO—, CH$_2$=C(CH$_3$)—COO—, CH$_2$C(Cl)—COO—,

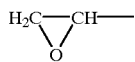

especially CH$_2$=CH—COO—;
- m, n each represent, independently, a whole number from 2 to 20, especially from 2 to 12.

The essential structural element of the compounds with formula I is a structural unit with formulae $a^1$ or $a^2$

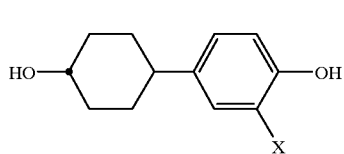

II wherein
- X represents halogen, —CH$_2$—CH=CH$_2$, —OR$^2$, —COOR$^2$, —COR$^2$, —OCOR$^2$; and
- $R^2$ represents $C_1$–$C_{20}$-alkyl, especially $C_1$–$C_{12}$-alkyl.

The compounds according to the invention, with formula I, can be readily synthesised using known methods, such as those of Schemes 1–5. Formation of links $Z^1$, $Z^2$, $Z^3$, for example, between the rings or ring systems A and B listed in formula I have been described on several occasions in the liquid crystal literature, and are well known to a person skilled in the art. A small quantity of 2,6-di-tert-butyl-4-methylphenol/"butyl hydroxytoluene" (BHT) is added to each stage to prevent undesirable thermal crosslinking.

Scheme 1
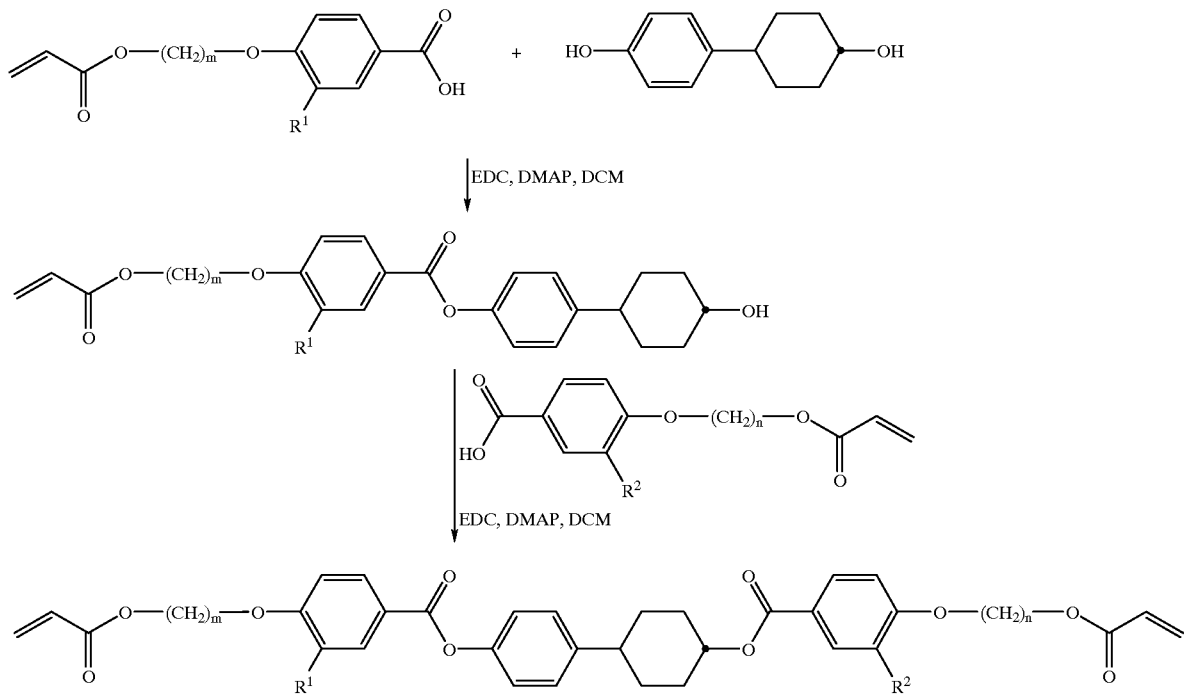
Scheme 2
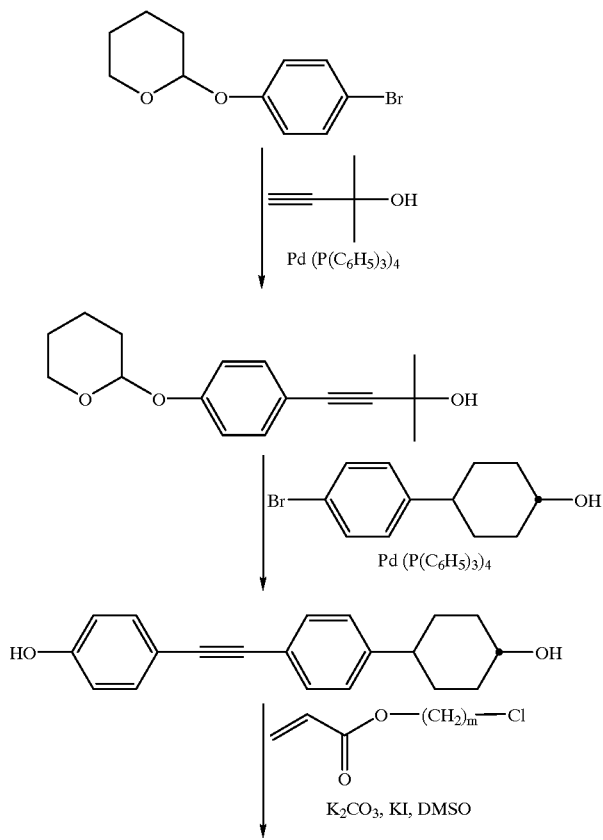

-continued
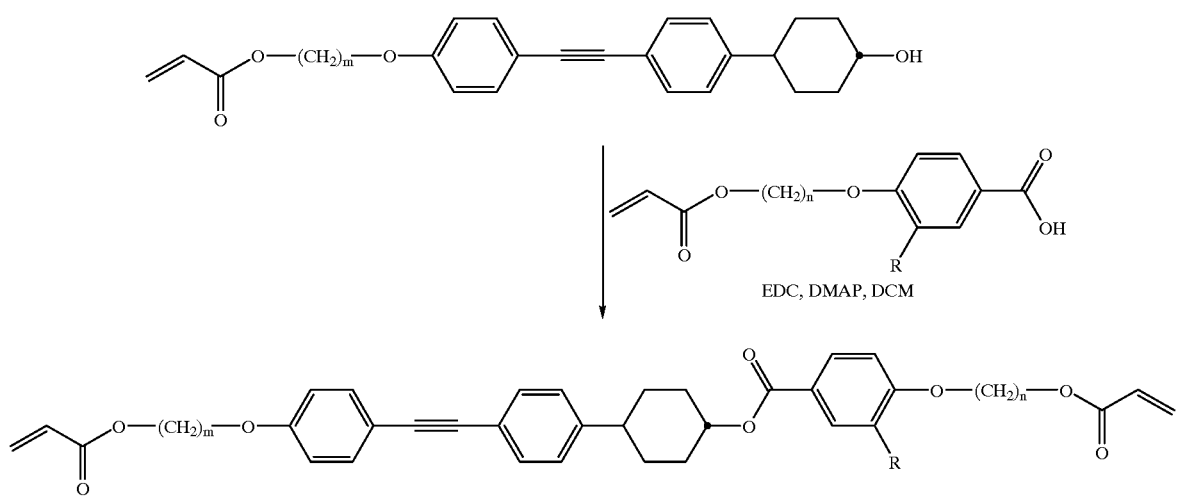
EDC, DMAP, DCM
Scheme 3
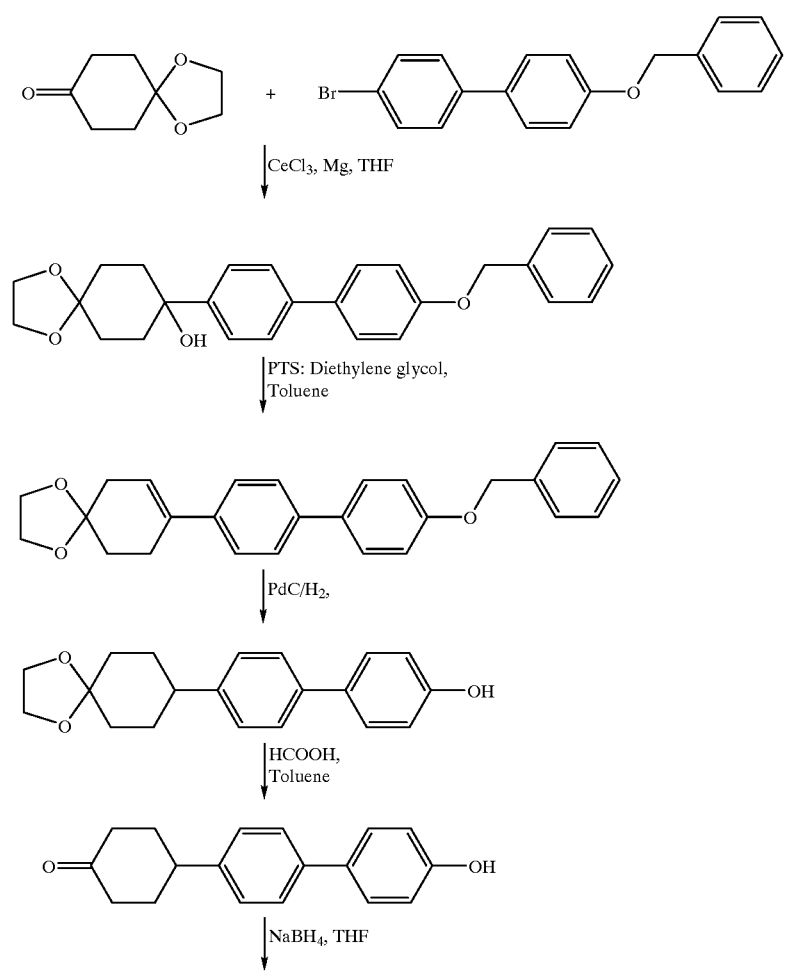

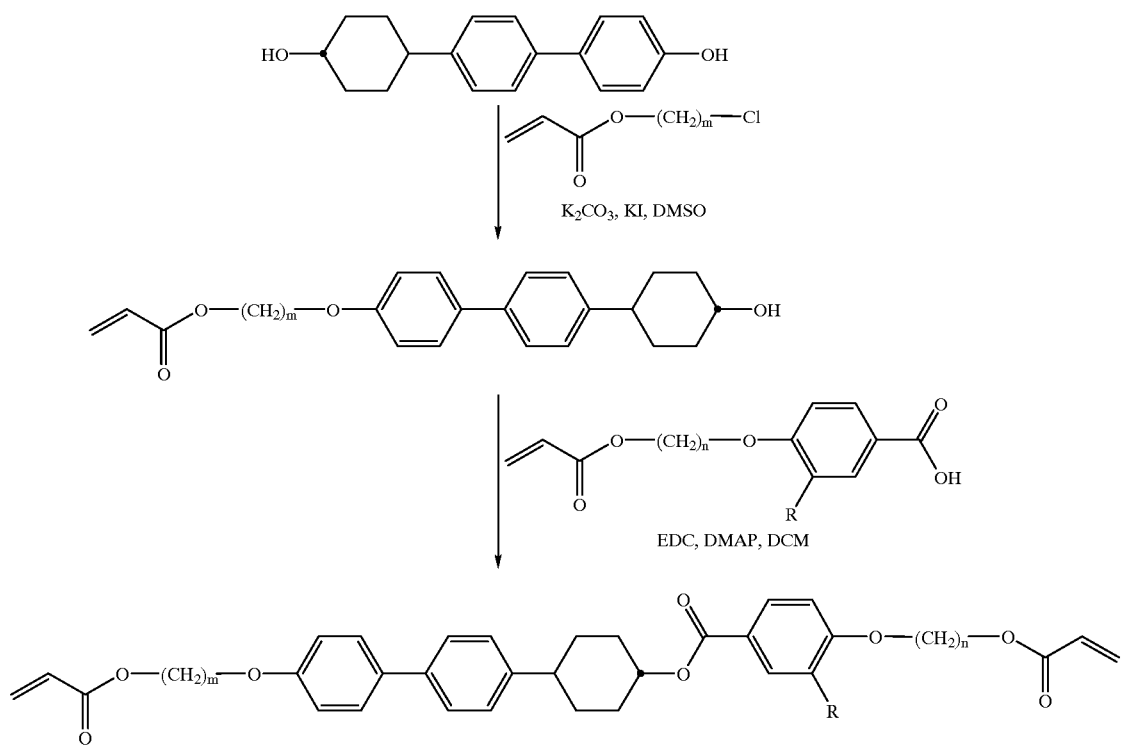
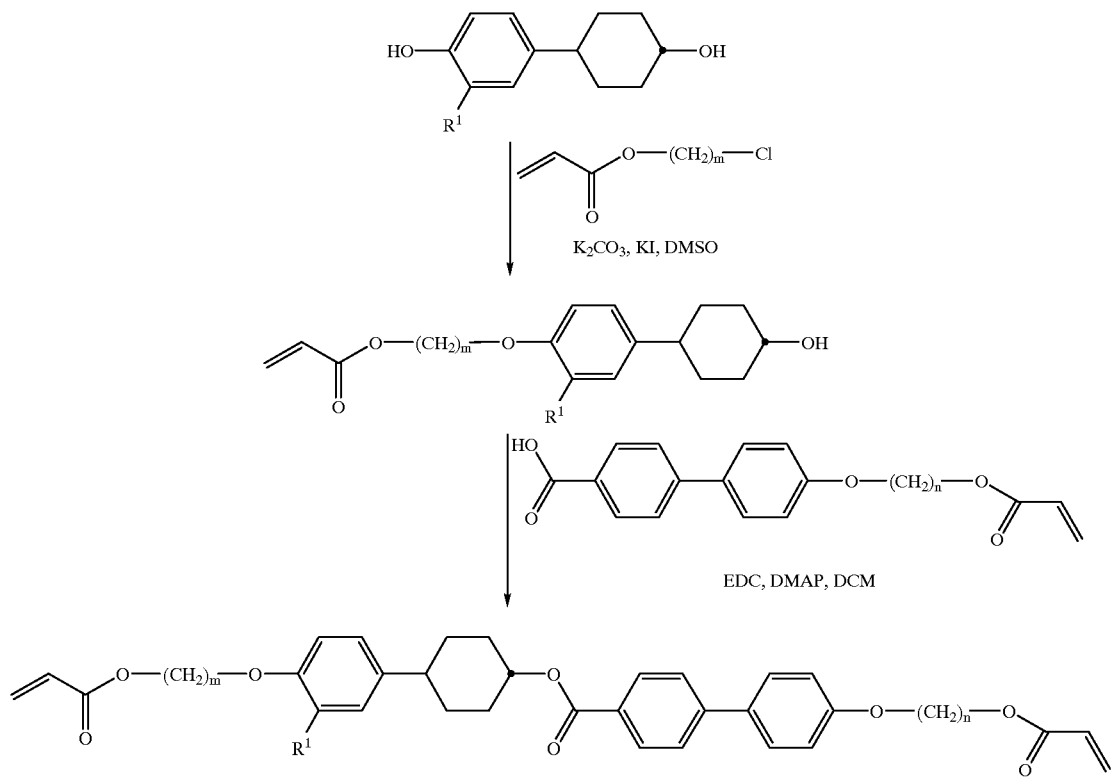
Scheme 4

Scheme 5
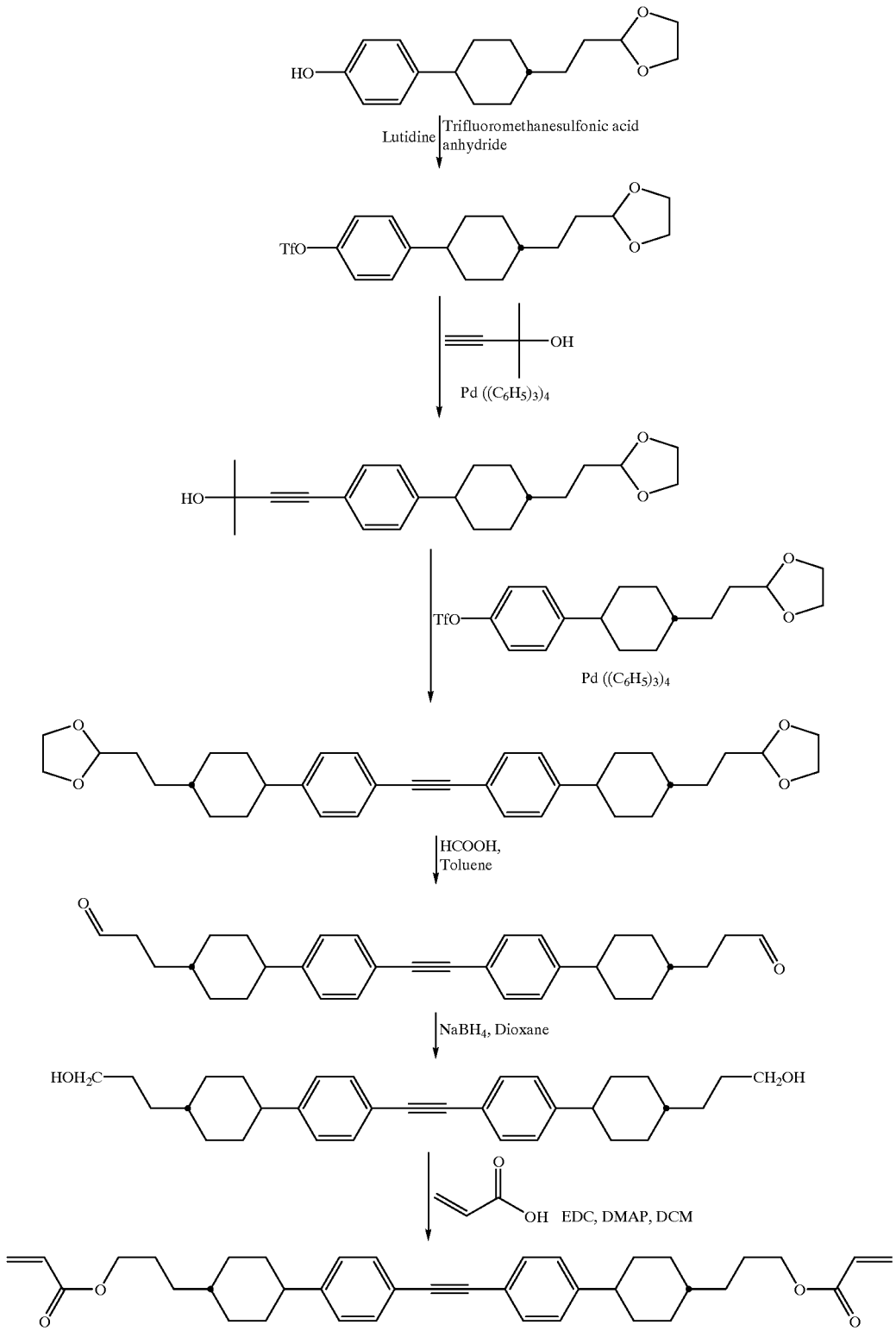
The compounds of formula I may be used alone, in the form of mixtures with other compounds of formula I or with other liquid crystal components. Preferred liquid crystalline mixtures contain at least two components. For liquid crystalline mixtures containing additional components other than compounds of formula I, it is preferred that these additional liquid crystalline components contain a photo-crosslinkable group. One or more chiral compounds may also be contained in the mixture.

The good solubility and miscibility of the compounds with Formula I means that liquid crystal mixtures containing a high proportion of compound of Formula I may be prepared. Such mixtures may contain up to 100% by weight of the compounds of formula I.

The mixtures according to the invention preferably contain not only one or more compounds with Formula I, but also one or more compounds from the group of compounds with the general formulae

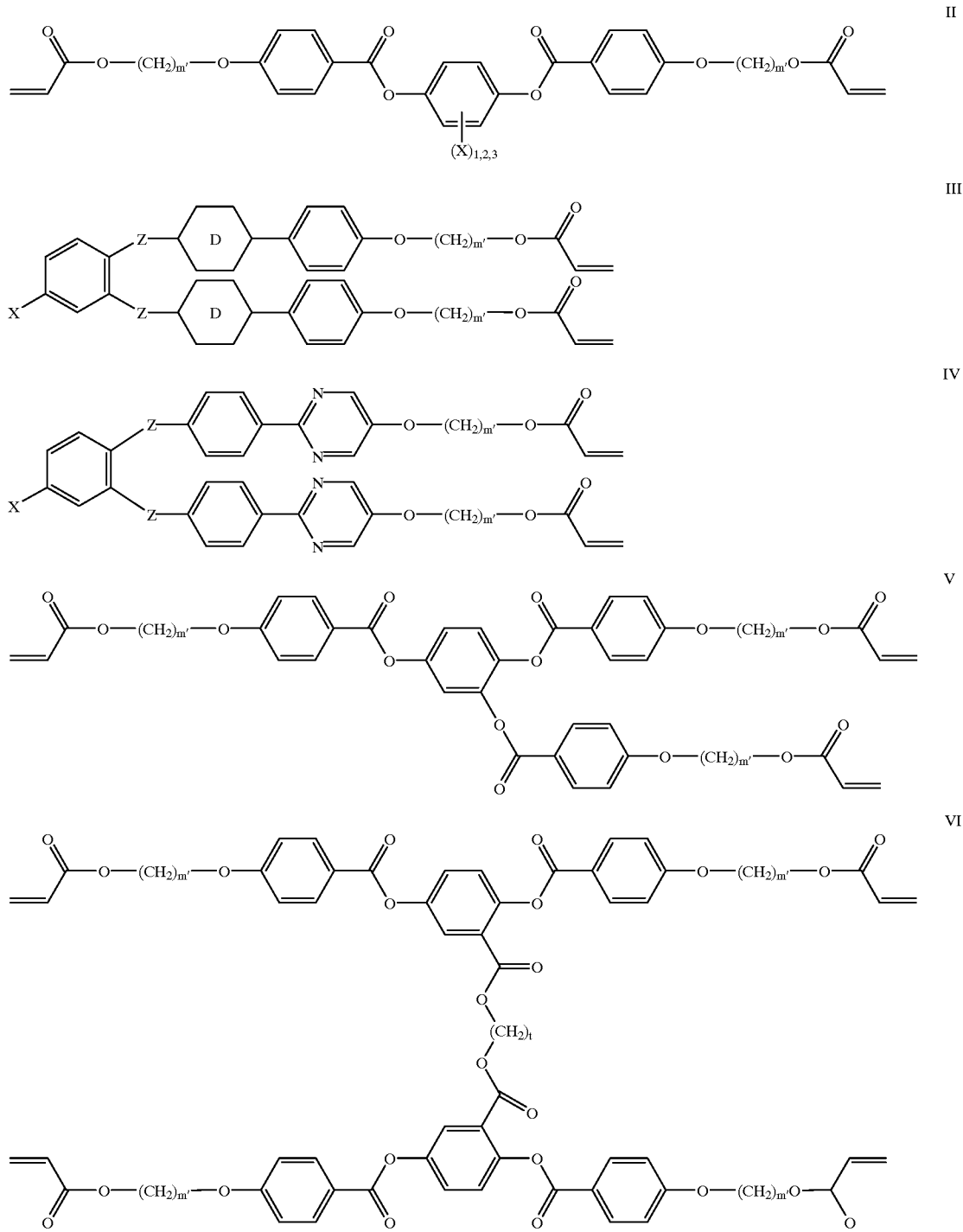

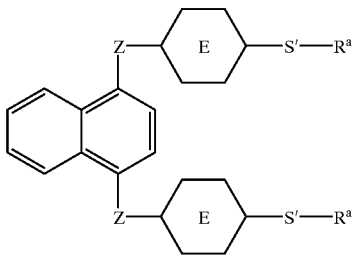

VII

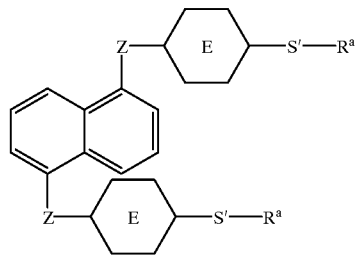

VIII wherein
- X represents hydrogen, $C_1$–$C_{20}$-alkyl, $C_1$–$C_{20}$-alkenyl, $C_1$–$C_{20}$-alkyloxy, $C_1$–$C_{20}$-alkyloxy carbonyl, formyl, $C_1$–$C_{20}$-alkyl carbonyl, $C_1$–$C_{20}$-alkyl carbonyloxy, fluorine, chlorine, bromine, cyano or nitro;
- m' represents a whole number from 2 to 20;
- t represents a whole number from 2 to 12;
- Z represents —COO—, —OOC—, —OCH$_2$—, —CH$_2$O—, —O(CH$_2$)$_3$—, —OOC(CH$_2$)$_2$—, —COO(CH$_2$)$_3$—;
- D represents 1,4-phenylene, trans-1,4-cyclohexylene, pyridine-2,5-diyl, pyrimidine-2,5-diyl or trans-1,4cyclohexylene-1,4-phenylene;
- E 1,4phenylene, or 2- or 3-fluoro-1,4phenylene;
- S' —(CH$_2$)$_m$— or —O(CH$_2$)$_m$—;
- R$^a$ represents crosslinkable groups with the structure CH$_2$=CH—, CH$_2$=CH—COO—, CH$_2$=C(CH$_3$)—COO—, CH$_2$=C(Cl)—COO—,

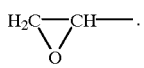

The manufacture of the compounds with Formula I and liquid crystalline mixtures containing these compounds are further illustrated by the following non-limiting examples. In the examples C represents a crystalline, N a nematic, S a smectic and I the isotropic phase.

EXAMPLE 1

Preparation of 4-(6-Acryloyloxyhexyloxy)benzoic Acid trans-4-[4-[4-(6-Acryloyloxy-hexyloxy)benzoyloxy]cyclohexyl]phenyl Ester

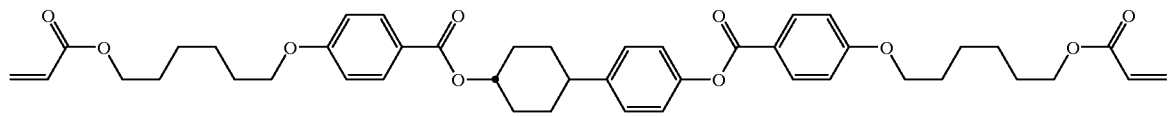

A solution of 48.0 g (250 mmols) N-(3-dimethylaminopropyl)-N'-ethylcarbodiimide hydrochloride (EDC) in 1 l DCM was added dropwise to a suspension of 19.2 g (100 mmols) 4-(trans-4-hydroxycyclohexyl)phenol, 73.0 g (250 mmols) 4-[6-acryloyl-hexyloxy] benzoic acid and 3.0 g (25 mmols) 4-dimethylaminopyridine (DMAP) in 0.65 l dichloromethane (DCM) at 0° C. over a period of one hour. It was stirred for a further hour at 0° C. and then over night at room temperature. The reaction mixture was then poured onto 1.5 l of semi-saturated NaCl solution and extracted three times with 0.6 l DCM. The combined organic phases were washed twice with 0.4 l of semi-saturated NaCl solution, dried over magnesium sulphate, filtered and concentrated. The residue was purified by chromatooraphy (column filled with 2.3 kg silica gel), using toluene/acetic acid 95:5 as eluant. Recrystallisation from toluene gave 12.3 g 4-(6-acryloyloxyhexyloxy)benzoic acid trans-4-[4-[4-(6-acryloyloxyhexyloxy)benzoyloxy]cyclohexyl]phenyl ester; melting point (C-$S_F$) 84° C., phase transitions ($S_F$-$S_G$) 107° C., ($S_G$-N) 162° C.

Asymmetric compounds containing phenyl ester residues which are variously substituted on both sides of the 4-(trans-4-hydroxycyclohexyl)phenol were prepared using a two-step synthesis analogous to that of Scheme 1. Mono-esterification of the more reactive phenolic hydroxy group of the 4-(trans-4-hydroxycyclohexyl)phenol and subsequent esterification with a differently substituted phenyl carbonic acid produced the asymmetrical substituted diester.

The following 4-(trans-4-hydroxycyclohexyl)-phenols mono-substituted in 2-position were prepared using a similar procedure.

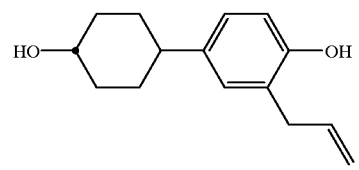

-continued

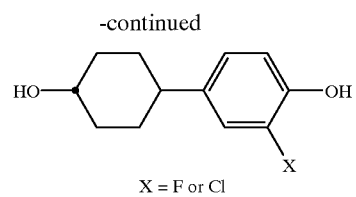

X = F or Cl

-continued

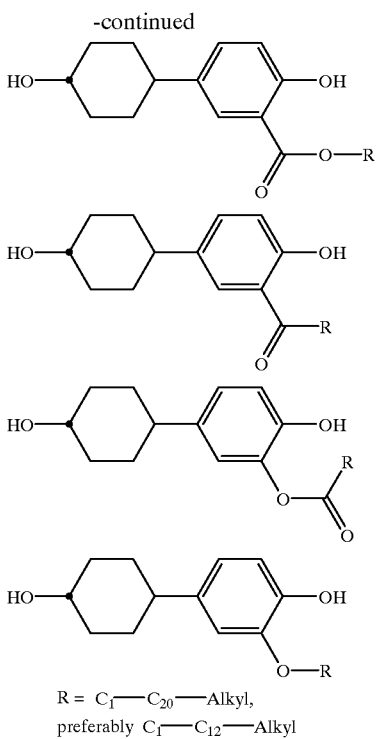

R = C$_1$—C$_{20}$—Alkyl,
preferably C$_1$—C$_{12}$—Alkyl

The substituted 4-(trans-4-hydroxycyclohexyl)phenols used as the raw material were manufactured, for example, by the following methods:
a) 2-Allyl-4-(trans-4-hydroxycyclohexyl)phenol

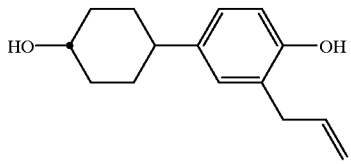

3.5 g of trans-4-(4-allyloxyphenyl)cyclohexanol was stirred for one hour under nitrogen at 240° C. After cooling, the reaction mixture was dissolved in approx. 100 ml of acetic ester and filtrated over a little silica gel. The solvent was removed and the residue was cleaned by recrystallisation from cyclohexane/tert.-butyl methyl ether, to give 2.9 g of 2-allyl-4-(trans-4-hydroxycyclohexyl)phenol.

The trans-4-(4-allyloxyphenyl)cyclohexanol used as raw material was manufactured by the following method:
trans-4-(4-Allyloxyphenyl)cyclohexanol

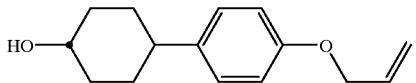

2.66 g (22 mmols) allyl bromide was added to a suspension of 3.84 g (20 mmols) p-(trans-4-hydroxycyclohexyl)phenol and 2.8 g (20.5 mmols) potassium carbonate in 40 ml of acetone. The resulting mixture was stirred under nitrogen with reflux over night. The mixture was then poured into 200 ml of water and extracted twice with 200 ml of diethyl ether. The combined organic phases were washed once with 100 ml 10% NaOH solution and once with 100 ml of water, dried over magnesium sulphate, filtered and concentrated by removal of solvent The residue was cleaned by recrystallisation from acetic ester, resulting in 3.7 g trans-4-(4-allyloxyphenyl)cyclohexanol.
b) 2-Fluoro-4-(trans-4-hydroxycyclohexyl)phenol

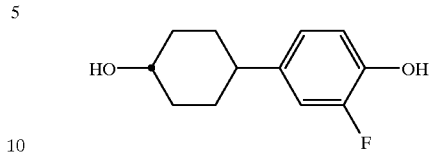

0.76 g (20 mmols) NaBH$_4$ was suspended in 30 ml THF under nitrogen and cooled to 0° C. A solution of 4.16 g 4-(3-fluoro-4-hydroxyphenyl)cyclohexanone in 50 ml THF was added dropwise at the same temperature over a period of 15 minutes, and the resulting mixture was stirred at 0° C. until no more of the starting material was present. 10 ml 25% HCl was then added dropwise at a temperature of between 0–10° C., and stirred for a further 30 minutes. The reaction mixture was then poured into 100 ml of water and extracted three times with 50 ml of diethyl ether. The combined organic phases were washed twice with 50 ml of water, dried over magnesium sulphate and filtered. Removal of the solvent and recrystallisation of the residue from isopropanol gave 2-fluoro-4-(trans-4-hydroxycyclohexyl)phenol.

The 4-(3-fluoro-4-hydroxyphenyl)cyclohexanone used as the raw material was manufactured by the following method:
8-(4-Benzyloxy-3-fluorophenyl)-1,4-dioxaspiro[4.5]decan-8-ol

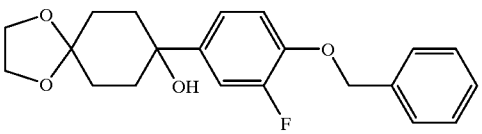

24.65 g (101 mmols) CeCl$_3$ was placed under nitrogen. 247 ml THF at 0° C. was added dropwise over a period of 30 minutes and the resulting suspension was stirred over night at room temperature. The next day a Grignard solution was prepared by the addition of approximately 10% of a solution containing 23.11 g (100 mmols) 1-benzyloxy-4-bromo-2-fluorobenzene in 100 ml THF to a mixture of 24.31 g (100 mmols) magnesium, a few grains of iodine. The reaction was started by heating with a hair dryer and as soon as reflux temperature was reached the remaining solution was added dropwise, over a period of about 40 minutes. The solution was stirred under reflux for a further 2 hours and then allowed to cool to room temperature.

The CeCl$_3$ solution manufactured the day before was cooled to 0° C., and the freshly manufactured Grignard solution was added over a period of 30 minutes at 0 to 5° C. The mixture was stirred for a further 2 hours at 0° C. and a solution of 21.08 g (135 mols) 1,4-dioxaspiro[4.5]decan-8-ol in 150 ml THF was then added dropwise at 0° C. The mixture was stirred over night at room temperature. The reaction mixture was poured on to 300 ml 10% glacial acetic acid, kept at 20° C. by the addition of a little ice and stirred for a further 20 minutes. The product was extracted three times with 250 ml of acetic ester. The combined organic phases were washed once with 250 ml of semi-saturated NaCl solution and once with 200 ml of saturated NaHCO$_3$ solution, dried over magnesium sulphate and filtered. Removal of the solvent gave the concentrated organic residue. The product was purified by column chromatography on silica gel, eluting with cyclohexane/acetic ester, to give the 8-(4-benzyloxy-3-fluorophenyl)-1,4-dioxaspiro[4.5]decan-8-ol product.

8-(4-Benzyloxy-3-fluorophenyl)-1,4-dioxaspiro[4.5]dec-7-ene

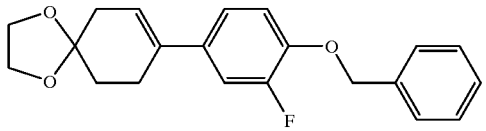

8-4-benzyloxy-3-fluorophenyl)-1,4-dioxaspiro[4.5]decan-8-ol, 9.93 g (160 mmols), diethylene glycol 28.67 g (80 mmols) and 0.76 g (4 mmols) p-toluene sulphonic acid were heated under reflux in 150 ml of toluene for one hour. The mixture was cooled and poured into 500 ml of saturated NaHCO$_3$ solution, and extracted three times with 200 ml of acetic ester. The combined organic phases were washed twice with 300 ml of semi-saturated NaCl solution and the solvent was removed to give a concentrated sample. The product, 8-(4-benzyloxy-3-fluorophenyl)-1,4-dioxaspiro[4.5]dec-7-ene was obtained by recrystallisation from tert.-butyl methyl ether.

4-(1,4-Dioxaspiro[4.5]dec-8-yl)-2-fluoro-4-phenol

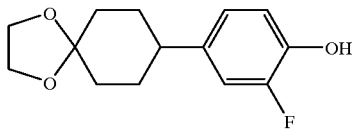

A mixture comprising 2 m of acetic acid and 23.83 g (70 mmols) of 8-(4-benzyloxy-3-fluorophenyl)-1,4-dioxaspiro[4.5]dec-7-ene in 200 ml of toluene was hydrated at room temperature in the presence of 2.38 g 10% palladium/C hydrating catalyst. After the hydrogen uptake was complete the reaction mixture was filtered through dicalcite. The solvent was removed to give the crude product. The product was purified by chromatography of the residue using silica gel and eluting with cyclohexane/acetic ester to give 4-(1,4-dioxaspiro[4.5]dec-8-yl)-2-fluoro-4-phenol.

4-(3-Fluoro-4-hydroxyphenyl)cyclohexanone

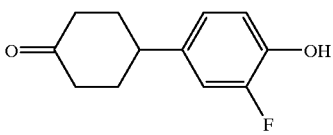

75 ml of formic acid was added to a solution of 16.40 g (65 mmols) of 4-(1,4-dioxaspiro[4.5]dec-8-yl)-2-fluoro-4-phenol in 150 ml toluene and stirred under nitrogen at 40° C. until no more of the starting material could be detected. The mixture was allowed to cool, the organic phase separated off and the aqueous phase extracted twice with 50 ml of toluene. The combined organic phases were washed once with 100 ml of saturated NaCl solution, and twice with 100 ml of NaHCO$_3$ solution. Removal of the solvent gave 4-(3-fluoro4-hydroxyphenyl)cyclohexanone.

2-chloro-4-(trans-4-hydroxycyclohexyl)phenol was manufactured by a similar method.

c) 2-Hydroxy-5-(trans-4-hydroxycyclohexyl)benzoic acid pentyl ester

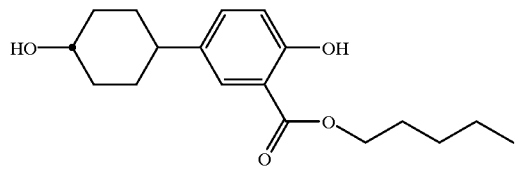

In an analogous fashion to Example 1b the product was prepared using 6.13 g (20 mmols) of 2-hydroxy-5-(4-oxocyclohexyl)benzoic acid pentyl ester and 0.76 g (200 mmols) NaBH$_4$. Recrystallisation from isopropanol gave the 2-hydroxy-5-(trans-4-hydroxycyclohexyl)benzoic acid pentyl ester product.

The hydroxy-5-(4-oxocyclohexyl)benzoic acid pentyl ester used as the raw material was manufactured by the following method:

4-(3-Acetyl-4-hydroxyphenyl)cyclohexanone

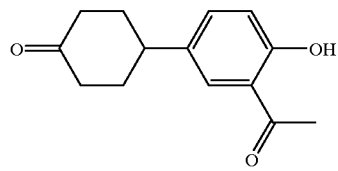

A solution of 9.31 g (118.6 mmols) acetyl chloride was added dropwise , at 0–5° C., over a period of 30 minutes to a suspension of 17.73 g (133 mmols) aluminium chloride in 150 ml DCM. A solution of 19.02 g (100 mmols) 4-(4-hydroxyphenyl)-cyclohexanone in 50 ml DCM was added dropwise to this mixture, also at a temperature of 0–5° C., over a period of 30 minutes. The resulting mixture was stirred for a further 90 minutes at this temperature until the starting material could no longer be detected.

The mixture was then poured on to 100 g of ice and 100 g of water, and vigorously stirred for one hour. The organic phase was separated off and the aqueous phase was extracted twice with 40 ml DCM. The combined organic phases were washed with 100 ml of saturated NaHCO$_3$ solution, dried over magnesium sulphate and filtered. Removal of the solvent gave the crude product as a residue. Recrystallisation of the crude product from ethanol gave 4-(3-acetyl-4-hydroxyphenyl)cyclohexanone.

2-Hydroxy-5-(4-oxocyclohexyl)benzoic acid

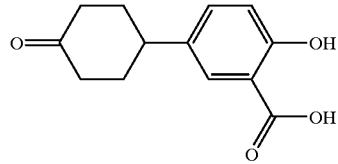

43.15 g (270 mmols) of bromine was added dropwise to a solution of 39.60 g (990 mmols) NaOH in 194 ml of water over a period of 30 minutes at 0–5° C., and stirred for a further hour at this temperature. 20.91 g (90 mmols) of 4-(3-acetyl-4-hydroxyphenyl)-cyclohexanone was dissolved at 70° C. in 100 ml of dioxane, allowed to cool to room temperature, and the emulsion formed was then added to alkali bromide solution. The reaction mixture was stirred for 3 hours at 40° C., and then over night at room temperature. 52 ml 37% HCl was added dropwise with slight cooling and the mixture was stirred for a further hour at room temperature. The precipitate was filtered off and washed with water. Recrystallisation from acetic ester gave 2-hydroxy-5-(4-oxocyclohexyl)benzoic acid.

2-Hydroxy-5-(4-oxocyclohexyl)benzoic acid pentyl ester

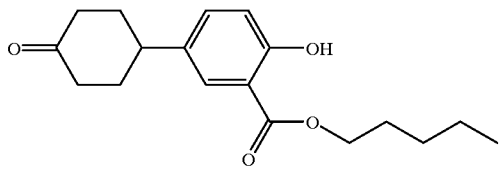

13.60 g (70 mmols) of 2-hydroxy-5-(4-oxocyclohexyl) benzoic acid was suspended in 90 ml of acetonitrile. 10.66 g (70 mmols) 1,8-diazabicyclo[5.4.0]undec-7-ene(1,5-5) (DBU) was added dropwise at 20° C. over a period of 10 minutes, followed by 11.63 g (77 mmols) pentyl bromide over a further period of 10 minutes. The suspension was then stirred under reflux for 18 hours. After cooling the reaction mixture was poured into 300 ml of water and extracted three times with 150 ml of acetic ester. The combined organic phases were washed once with 200 ml 1N HCl, three times with 150 ml of water, dried over magnesium sulphate and filtered. Removal of the solvent gave the crude product which was purified by chromatography on silica gel, eluting with cyclohexane/acetic ester to give 2-hydroxy-5-(4-oxocyclohexyl)benzoic acid pentyl ester.

The following compounds were manufactured in a similar fashion:

| R | $S^1$ | A—$Z^1$ | B | $S^2$ | R | Phase transitions |
|---|---|---|---|---|---|---|
| acrylate | $(CH_2)_4O$ | 4-methylcyclohexyl-CO-O-phenyl-4-methyl | 4-methylphenyl-CO-O-phenyl | $O(CH_2)_4$ | acrylate | Smp. (C—$S_F$) 81° C., $S_F$—$S_C$ 104° C., $S_C$—N 140° C. |
| acrylate | $(CH_2)_5O$ | 4-methylcyclohexyl-CO-O-phenyl-4-methyl | 4-methylphenyl-CO-O-phenyl | $O(CH_2)_5$ | acrylate | |
| acrylate | $(CH_2)_7O$ | 4-methylcyclohexyl-CO-O-phenyl-4-methyl | 4-methylphenyl-CO-O-phenyl | $O(CH_2)_7$ | acrylate | Smp. (C—$S_F$) 84° C., $S_F$—$S_B$ 96° C., $S_B$—$S_C$ 114° C., $S_C$—N 165° C. |
| acrylate | $(CH_2)_8O$ | 4-methylcyclohexyl-CO-O-phenyl-4-methyl | 4-methylphenyl-CO-O-phenyl | $O(CH_2)_8$ | acrylate | |
| acrylate | $(CH_2)_6O$ | 4-methylcyclohexyl-CO-O-phenyl-4-methyl | 4-methylphenyl-CO-O-(2-allyl)phenyl | $O(CH_2)_6$ | acrylate | Smp. (C—N) 95° C., Klp. (N—I) 136° C. |
| acrylate | $(CH_2)_6O$ | 4-methylcyclohexyl-CO-O-phenyl-4-methyl | 4-methylphenyl-CO-O-(2-fluoro)phenyl | $O(CH_2)_6$ | acrylate | |

-continued
| R | S¹ | A—Z¹ | B | S² | R | Phase transitions |
|---|---|---|---|---|---|---|
| 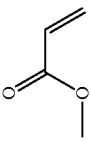 | (CH₂)₆O | 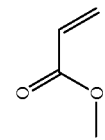 | 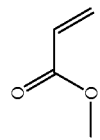 | O(CH₂)₆ | 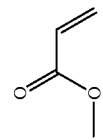 | |
| 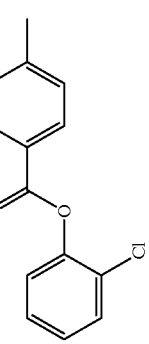 | (CH₂)₆O | 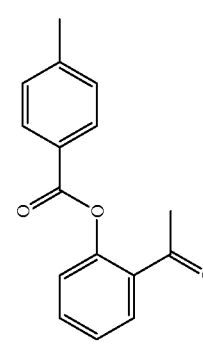 | 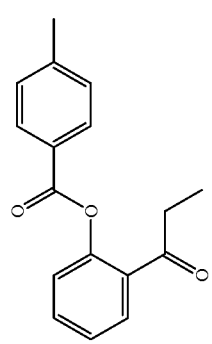 | O(CH₂)₆ | 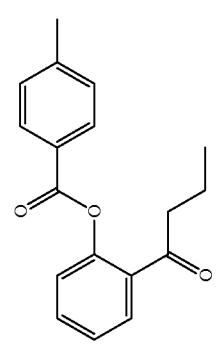 | |
| 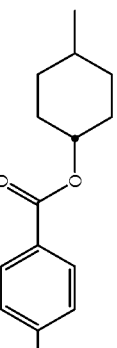 | (CH₂)₆O | | 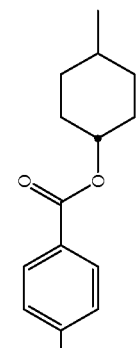 | O(CH₂)₆ | | |
| 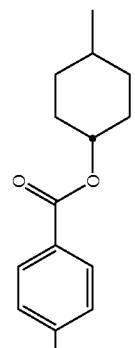 | (CH₂)₆O | | 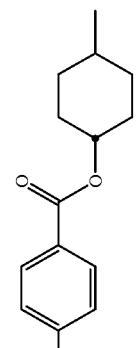 | O(CH₂)₆ | | |

| R | S¹ | A—Z¹ | B | S² | R | Phase transitions |
|---|---|---|---|---|---|---|
| acrylate | (CH₂)₆O | Me-cyclohexyl-O-C(O)-C₆H₄-Me | Me-C₆H₄-C(O)O-C₆H₄-C(O)-butyl | O(CH₂)₆ | acrylate | |
| acrylate | (CH₂)₆O | Me-cyclohexyl-O-C(O)-C₆H₄-Me | Me-C₆H₄-C(O)O-C₆H₄-C(O)-pentyl | O(CH₂)₆ | acrylate | |
| acrylate | (CH₂)₆O | Me-cyclohexyl-O-C(O)-C₆H₄-Me | Me-C₆H₄-C(O)O-C₆H₄-C(O)OMe | O(CH₂)₆ | acrylate | |
| acrylate | (CH₂)₆O | Me-cyclohexyl-O-C(O)-C₆H₄-Me | Me-C₆H₄-C(O)O-C₆H₄-C(O)OEt | O(CH₂)₆ | acrylate | |

-continued
| R | S¹ | A—Z¹ | B | S² | R | Phase transitions |
|---|---|---|---|---|---|---|
| 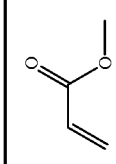 | (CH₂)₆O | 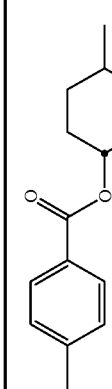 | 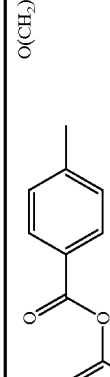 | O(CH₂)₆ | 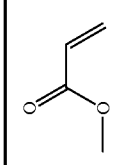 | |
|  | (CH₂)₆O |  | 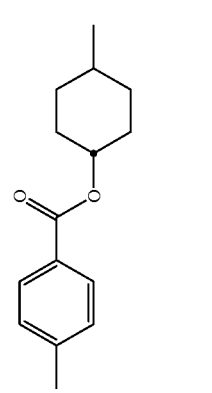 | O(CH₂)₆ | 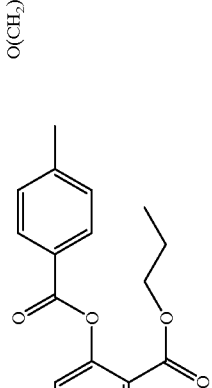 | |
| 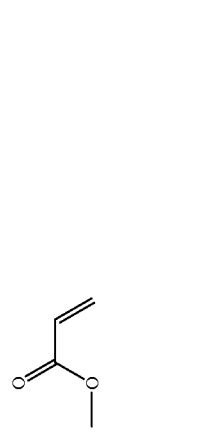 | (CH₂)₆O | 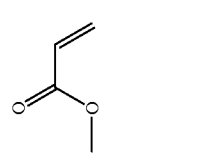 |  | O(CH₂)₆ |  | |
| 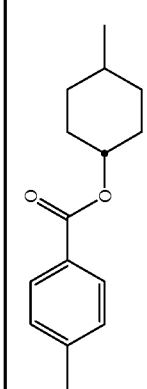 | (CH₂)₆O | 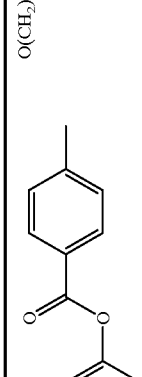 | 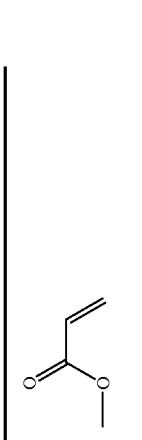 | O(CH₂)₆ | 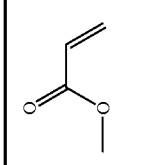 | |

-continued

| R | S¹ | A—Z¹ | B | S² | R | Phase transitions |
|---|---|---|---|---|---|---|
| acrylate | (CH₂)₆O | cyclohexyl-benzoate-methyl | 2-methoxyphenyl benzoate-methyl | O(CH₂)₆ | acrylate | |
| acrylate | (CH₂)₆O | cyclohexyl-benzoate-methyl | 2-ethoxyphenyl benzoate-methyl | O(CH₂)₆ | acrylate | |
| acrylate | (CH₂)₆O | cyclohexyl-benzoate-methyl | 2-pentyloxyphenyl benzoate-methyl | O(CH₂)₆ | acrylate | |
| acrylate | (CH₂)₆O | cyclohexyl-benzoate-methyl | phenyl 3-methoxy-4-methylbenzoate | O(CH₂)₆ | acrylate | Smp. (C—S$_C$) 74.3° C.<br>S$_C$—S$_A$ 104.5° C.<br>S$_A$—N 116.0° C.<br>Klp. (N-I) 176.3° C. |
| acrylate | (CH₂)₆O | cyclohexyl-benzoate-methyl | phenyl 3-ethoxy-4-methylbenzoate | O(CH₂)₆ | acrylate | Smp. (C—S$_C$) 84.8° C.<br>S$_C$—N = 76.0° C.<br>Klp. (N-I) 157.0° C. |

-continued
| R | S¹ | A—Z¹ | B | S² | R | Phase transitions |
|---|---|---|---|---|---|---|
| 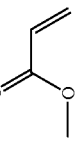 | (CH₂)₆O | 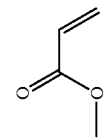 | 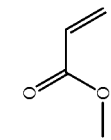 | O(CH₂)₆ | 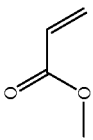 | |
| 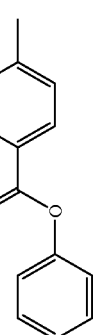 | (CH₂)₆O | 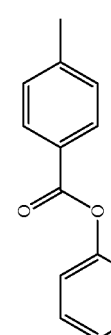 | 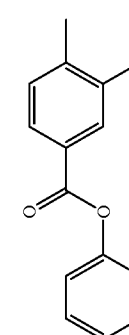 | O(CH₂)₆ | 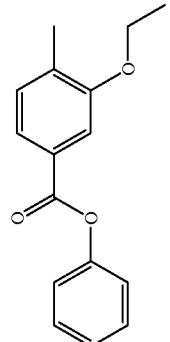 | |
| 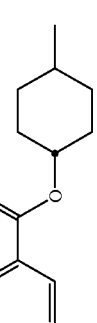 | (CH₂)₆O | 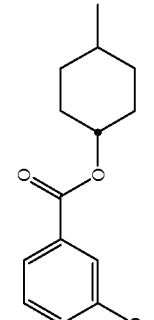 | 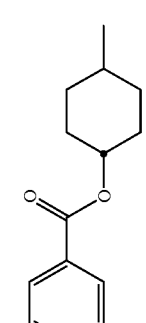 | O(CH₂)₆ | 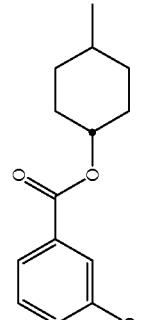 | Smp. (C—N) 116.0° C. Klp. (N—I) 129.4° C. |
|  | (CH₂)₆O |  |  | O(CH₂)₆ |  | Smp. (C—N) 86.3° C. Klp. (N—I) 99.9° C. |

EXAMPLE 2

4-(6-Acryloyloxyhexyloxy)benzoic Acid trans-4-[4-[4-(6-Acryloyloxyhexyloxy)phenyl-ethynyl]phenyl] cyclohexyl Ester

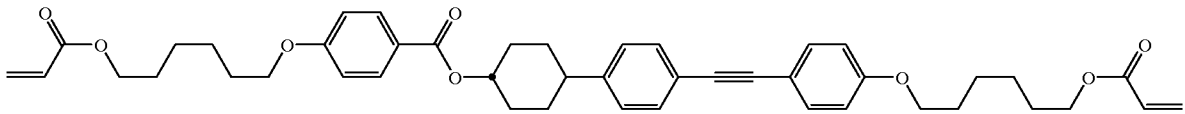

Using the same procedure as that set out in Example 1, 4.47 g (10 mmols) acrylic acid trans-6-[4-[4-hydroxycyclohexyl)phenylethynyl]phenoxy]hexyl ester, 3.22 g (11 mmols) of 4-[6-acryloyloxy]benzoic acid, 0.13 g (1.1 mmol) DMAP and 2.11 g (11 mmol) EDC were reacted together. Chromatographic cleaning of the residue on silica gel, eluting with toluene/acetic ester 95:5 and recrystallisation from toluene gave 4-(6-acryloyloxyhexyloxy)benzoic acid trans-4-[4-[4-(6-acryloyloxyhexyloxy)phenyl-ethynyl]phenyl]cyclohexyl ester.

The acrylic acid trans-6-[4-[4-(4-hydroxycyclohexyl) phenylethynyl]phenoxy]-hexyl ester starting material was manufactured using a known method (A. Carpita, A. Lessi, R. Rossi, Synthesis Communications 1984, 571) from 4-ethynyl-phenol and trans-4-(4-bromophenyl)-cyclohexanol, followed by esterification with acrylic acid 6-chlorohexyl ester (cf. Scheme 2).

The following compounds were manufactured using a similar procedure.

-continued

| R | S¹ | A—Z¹ | B | S² | R | Phase Transition |
|---|---|---|---|---|---|---|
| (acrylate) | (CH₂)₆O | (ethoxy-methyl-benzoate-cyclohexyl) | (phenyl-alkyne-phenyl) | O(CH₂)₆ | (acrylate) | |

EXAMPLE 3

4-(6-Acryloyloxyhexyloxy)benzoic Acid trans-4-[4'-(6-Acryloyloxyhexyloxy0)biphenyl-4-yl]cyclohexyl Ester

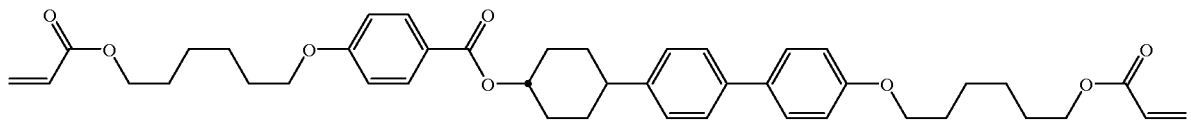

Using the same procedure set out in Example 1, 4.23 g (10 mmols) acrylic acid trans-6-[4'(4-hydroxycyclohexyl)-biphenyl-4-yloxyl]hexyl ester, 3.22 g (11 mmols) 4-[6-acryloyloxy]benzoic acid, 0.13 g (1.1 mmol) DMAP and 2.11 g (11 mmols) EDC were reacted together. The crude product was purified by chromatographic cleaning of the residue on silica gel with toluene/acetic ester 95:5 as eluant. The 4-(6-acryloyloxyhexyloxy)benzoic acid trans-4-[4'-(6-acrylyloxyhexyloxy)biphenyl-4-yl]cyclohexyl ester product was isolated by recrystallisation from toluene.

The acrylic acid trans-6-4'-(4-hydroxycyclohexyl) biphenyl-4-yloxyl]hexyl ester starting material was prepared using known methods by the Grignard coupling of 4-(4-bromophenyl)phenol and 1,4-dioxaspiro[4.5]decan-8-one (similar to Example 1b), followed by reduction of the keto group and Williamson etherification of the phenolic hydroxy group with acrylic acid 6-chlorohexyl ester (cf. Scheme 3).

The following compounds are prepared using similar methods.

| R | S¹ | A—Z¹ | B | S² | R | Phase Transition |
|---|---|---|---|---|---|---|
| (acrylate) | (CH₂)₃O | (methyl-benzoate-cyclohexyl) | (biphenyl) | O(CH₂)₃ | (acrylate) | |
| (acrylate) | (CH₂)₄O | (methyl-benzoate-cyclohexyl) | (biphenyl) | O(CH₂)₄ | (acrylate) | |
| (acrylate) | (CH₂)₅O | (methyl-benzoate-cyclohexyl) | (biphenyl) | O(CH₂)₅ | (acrylate) | |
| (acrylate) | (CH₂)₇O | (methyl-benzoate-cyclohexyl) | (biphenyl) | O(CH₂)₇ | (acrylate) | |

| R | S¹ | A—Z¹ | B | S² | R | Phase Transition |
|---|---|---|---|---|---|---|
| acryloyl | (CH₂)₈O | benzoate-cyclohexyl | biphenyl | O(CH₂)₈ | acryloyl | |
| acryloyl | (CH₂)₆O | methoxy-benzoate-cyclohexyl | biphenyl | O(CH₂)₆ | acryloyl | |
| acryloyl | (CH₂)₆O | ethoxy-benzoate-cyclohexyl | biphenyl | O(CH₂)₆ | acryloyl | |

EXAMPLE 4

4'-(6-Acryloyloxyhexyloxy)biphenyl-4-carbonic Acid trans-4-[4-(6-acryloyloxyhexyloxy)-phenyl]cyclohexyl Ester

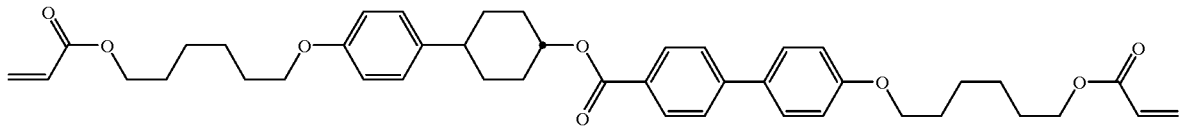

Using the procedure set out in Example 1, 3.46 g (10 mmols) of acrylic acid trans-6-[4-((4-hydroxycyclohexyl)phenoxy]hexyl ester, 3.68 g (910 mmols) 4'-(6-acryloyloxyhexyloxy) biphenyl-4-carbonic acid, 0.12 g (1 mmol) DMAP and 2.11 g (11 mmols) EDC were reacted together. The resulting product was purified by chromatographic cleaning of the residue on silica gel with cyclohexane/acetic ester (4:1) as eluant. The product was isolated by recrystallisation from acetone/ethanol (1:2) to give 4'-(6-acryloyloxy-hexyloxy)biphenyl-4-carbonic acid trans-4-[4-(6-acryloyloxyhexyloxy)phenyl]cyclohexyl ester (melting point (C-S$_x$) 75.3° C., polymerisation at T<150° C.).

The acrylic acid trans-6-[4-(4-hydroxycyclohexyl)phenoxy]hexyl ester starting material was obtained by Williamson etherification of 4-(trans-4-hydroxycyclohexyl)-phenol with acrylic acid 6-chlorohexyl ester (cf. Scheme 4). The substituted 4-(trans-4-hydroxycyclohexyl)phenols mentioned in Example 1 were also similarly alkylated.

The following compounds were prepared using similar methods.

| R | S¹ | A—Z¹ | B | S² | R | Phase Transition |
|---|---|---|---|---|---|---|
| acryloyl | (CH₂)₃O | phenyl-cyclohexyl ester | biphenyl | O(CH₂)₃ | acryloyl | |

-continued

| R | S¹ | A—Z¹ | B | S² | R | Phase Transition |
|---|---|---|---|---|---|---|
| acrylate | (CH₂)₄O | phenyl-cyclohexyl-O-C(O)- | biphenyl | O(CH₂)₄ | acrylate | |
| acrylate | (CH₂)₅O | phenyl-cyclohexyl-O-C(O)- | biphenyl | O(CH₂)₅ | acrylate | |
| acrylate | (CH₂)₇O | phenyl-cyclohexyl-O-C(O)- | biphenyl | O(CH₂)₇ | acrylate | |
| acrylate | (CH₂)₈O | phenyl-cyclohexyl-O-C(O)- | biphenyl | O(CH₂)₈ | acrylate | |
| acrylate | (CH₂)₆O | allyl-phenyl-cyclohexyl-O-C(O)- | biphenyl | O(CH₂)₆ | acrylate | |
| acrylate | (CH₂)₆O | F-phenyl-cyclohexyl-O-C(O)- | biphenyl | O(CH₂)₆ | acrylate | |
| acrylate | (CH₂)₆O | Cl-phenyl-cyclohexyl-O-C(O)- | biphenyl | O(CH₂)₆ | acrylate | |
| acrylate | (CH₂)₆O | acetyl-phenyl-cyclohexyl-O-C(O)- | biphenyl | O(CH₂)₆ | acrylate | |

| R | S¹ | A—Z¹ | B | S² | R | Phase Transition |
|---|---|---|---|---|---|---|
| ![acrylate] | (CH₂)₆O | [substituted phenyl-cyclohexyl with ethyl ester] | biphenyl | O(CH₂)₆ | acrylate | |
| ![acrylate] | (CH₂)₆O | [substituted phenyl-cyclohexyl with pentyl ester] | biphenyl | O(CH₂)₆ | acrylate | |
| ![acrylate] | (CH₂)₆O | [substituted phenyl-cyclohexyl with pentyloxy] | biphenyl | O(CH₂)₆ | acrylate | |

EXAMPLE 5

Acrylic Acid 3-[Trans-4-[4-[trans-4-(3-acryloyloxypropyl)cyclohexyl]phenylethynyl]-phenyl]cyclohexyl]propyl Ester

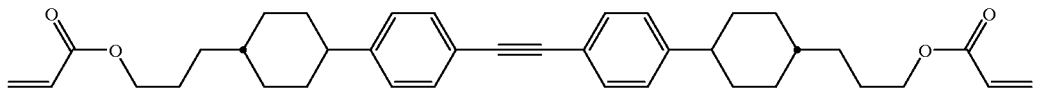

Using the procedure set out in Example 1, 2.29 g (5 mmols) of 3-[trans-4-[4-[4-[trans-4-(3-hydroxypropyl) cyclohexyl]phenylethynyl]phenyl]cyclohexyl]-propan-1-ol, 1.08 g (15 mmols) acrylic acid, 0.18 g (1.5 mmol) DMAP and 2.88 g (15 mmols) EDC were reacted together. The crude product was purified by chromatographic cleaning of the residue on silica gel with cyclohexane/acetic ester (4:1) eluant. The product was isolated by recrystallisation from acetone/ethanol (1:2) to give acrylic acid 3-[trans-4-[4-[4-[trans-4-(3-acryloyloxypropyl)cyclohexyl]phenylethynyl] phenyl]cyclohexyl]-propyl ester.

The 3-[trans4-[4-[trans-4-(3-hydroxypropyl) cyclohexyl]phenylethynyl]-phenyl]cyclohexyl]propan-1-ol starting material was manufactured from 4-(4-hydroxy-phenyl)cyclohexanone. The required chain length of the spacer was first synthesised by a Wittig reaction, followed by catalytic hydration of the double bond formed. The phenolic hydroxy group was then transferred to the corresponding triflate which was then coupled to the diaryl acetylene using known methods (A. Carpita, A. Lessi, R. Rossi, Synthesis Communications 1984, 571). Acid catalysed splitting of the dioxolane protection groups, followed by reduction with sodium borohydride, gave the required dialcohol (cf. Scheme 5).

The following compounds were prepared using similar methods.

| R | S¹ | A—Z¹ | B | S² | R |
|---|---|---|---|---|---|
| ![acrylate] | (CH₂)₄ | cyclohexyl-phenyl-ethynyl | phenyl-cyclohexyl | (CH₂)₄ | acrylate |

| R | S¹ | A—Z¹ | B | S² | R |
|---|---|---|---|---|---|
| (acrylate) | $(CH_2)_5$ | cyclohexyl-phenyl-C≡C- | biphenyl | $(CH_2)_5$ | (acrylate) |
| (acrylate) | $(CH_2)_6$ | cyclohexyl-phenyl-C≡C- | biphenyl | $(CH_2)_6$ | (acrylate) |
| (acrylate) | $(CH_2)_7$ | cyclohexyl-phenyl-C≡C- | biphenyl | $(CH_2)_7$ | (acrylate) |

EXAMPLE 6

A mixture of 64% by weight of 4-(6-acryloyloxyhexyloxy)benzoic acid, 4-[4-(6-acryloyloxyhexyloxy)benzoyloxy]-2-pentyloxycarbonylphenyl ester, 20% by weight of 4-(6-acryloyloxyhexyloxy)benzoic acid trans-4-[4-(6-acryloyloxyhexyloxy) benzoyloxy]cyclohexyl]phenyl ester, 12% by weight of 4-(6-acryloyloxyhexyloxy)-benzoic acid 4-[4-6-acryloyloxyhexyloxy)benzoyloxyl]-2-methylphenyl ester and 4% by weight of 4-(6-acryloyloxyhexyloxy) benzoic acid 4-[4-(6-acryloyloxyhexyloxy)benzoyl-oxy]-2-chlorophenyl ester was prepared. 2% by weight of a photoinitiator (IRGACURE, Ciba-Geigy) and 2% by weight of inhibitor (BHT) were added thereto. The resulting mixture was dissolved in anisole (20% by weight), then spin-coated at 900 revolutions per minute on to a glass substrate that was coated with rubbed polyimide (SE 510, NISSAN). The layer was crosslinked in the vacuum cabinet at room temperature in a vacuum with xenon light (e.g. 30 minutes). A parallel orientated nematic layer with a layer thickness of 1 μm and a birefringence of approx. 0.15 was produced. This layer acts as an optical retarder.

EXAMPLE 7

2% by weight of IRGACURE and 2% by weight of BHT was added to a mixture having the same composition as that specified in Example 6. The resulting mixture was dissolved in anisole (20% by weight), spin coated at 900 revolutions per minute on to a glass sheet pre-coated with an orientation layer of methacryloyloxyethyl-3-(E)-[4-cyano-4'-biphenyl] acrylate, which forms a photo polymerisable network (PPN). This orientation layer has a predetermined pattern photolithographically formed by illuminating with linearly polarised light through a mask. The new layer (on the PPN layer) was dried at 40° C. on a heating bench, then exposed in the vacuum cabinet at room temperature in a vacuum with xenon light. The registered original structure was maintained and accurately incorporated in the new network. A clear birefringence (Δn) was detectable. This layer acts as a spatially structured optical retarder.

What is claimed is:

1. A compound of the formula I:

$$R-S^1-A-Z^1-B-S^2-R \qquad I$$

where
A and B are each an independent ring system and each have the formulae a¹, a² or b,

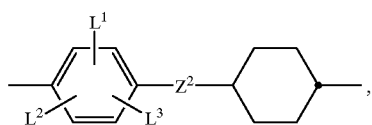
a¹

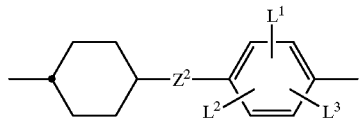
a²

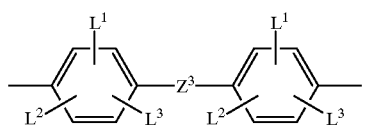
b whereby, in the trans-1,4-cyclohexylene ring, one or two non-adjacent $CH_2$ groups may be replaced by oxygen, and whereby, in the 1,4-phenylene ring, one or two non-adjacent CH groups may be replaced by nitrogen;

$L^1$, $L^2$, $L^3$ represent, independently, hydrogen, $C_1$–$C_{20}$-alkyl, $C_1$–$C_{20}$-alkenyl, $C_1$–$C_{20}$-alkyloxy, $C_1$–$C_{20}$-alkyloxy carbonyl, formyl, $C_1$–$C_{20}$-alkyl carbonyl, $C_1$–$C_{20}$-alkyl carbonyloxy, halogen, cyano or nitro;

$Z^1$, $Z^2$, $Z^3$ represent, independently, a single bond, —$CH_2CH_2$—, —$CH_2O$—, —$OCH_2$—, —COO—, —OOC—, —$(CH_2)_4$—, —$O(CH_2)_3$—, —$(CH_2)_3O$— or —C≡C—;

$S^1$, $S^2$ each independently represent a straight chain or branched alkylene grouping —$(CH_2)_r$, unsubstituted or substituted singly or multiply with fluorine, or —$((CH_2)_2$—$O)_r$—, or a chain with the formula —$(CH_2)_r$—Y—$(CH_2)_s$—, where Y represents a single bond or the linking functional group —O—, —COO—, —OOC—, —$NR^1$—, $NR^1$—CO—, —CO—$NR^1$—, $NR^1$—COO—, —OCO—$NR^1$—, $NR^1$, —CO—$NR^1$—, —O—OC—O—, —CH=CH—, or —C≡C—; where $R^1$ represents hydrogen or low alkyl, and where r and s each represent a whole number from 0 to 20 on condition that $2 \leq (r+s) \leq 20$;

R represents a crosslinkable group with the structure $CH_2$=CHCOO—, $CH_2$=C($CH_3$)—COO—, $CH_2$=C (Cl)COO—, $CH_2$=C(Ph)—COO—, $CH_2$=CH—COO—Ph—, $CH_2$=CH—CO—NH—, $CH_2$=C($CH_3$)—CONH—, $CH_2$=C(Cl)—CONH—, $CH_2$=C(Ph)—CONH—, $CH_2$=C(COOR')—$CH_2$—COO—, $CH_2$=CH—OOC—, Ph—CH=CH—, $CH_3$—C(=NR')—, cis or trans-HOOC—R'=CR'—COO—,

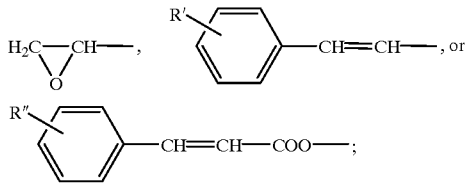

Ph reresents phenyl;
R' represents methyl, ethyl, propyl, butyl or pentyl, and
R" represents methyl, methoxy, cyano or halogen,
with the proviso that at least one of the ring systems A or B represents a ring system with the formula $a^1$ or $a^2$, at least one of $Z^1$ and $Z^2$ represent a single bond, and —R—$S^1$ and R—$S^2$ do not contain —O—O or —N—O— groups.

2. A compound of the formula I:

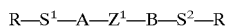     I where

A and B are each independent ring system and each have the formula $a^1$, $a^2$ or b,

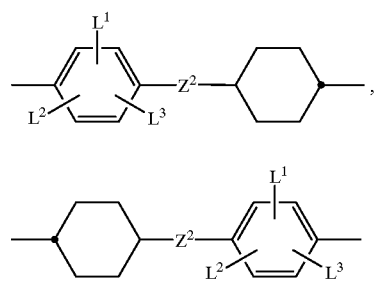

$a^1$ $a^2$

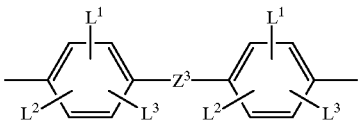

b whereby, in the trans-1,4-cyclohexylene ring, one or two non-adjacent $CH_2$ groups may be replaced by oxygen, and whereby, in the 1,4-phenylene ring, one or two non-adjacent CH groups may be replaced by nitrogen;

$L^1$, $L^2$, $L^3$ represent, independently, hydrogen, $C_1$–$C_{20}$-alkyl, $C_1$–$C_{20}$-alkenyl, $C_1$–$C_{20}$-alkyloxy, $C_1$–$C_{20}$-alkyloxy carbonyl, formyl, $C_1$–$C_{20}$-alkyl carbonyl, $C_1$–$C_{20}$-alkyl carbonyloxy, halogen, cyano or nitro;

$Z^1$, $Z^2$, $Z^3$ represent, independently, a single bond, —$CH_2CH_2$—, —$CH_2O$—, —$OCH_2$—, —COO—, —OOC—, —$(CH_2)_4$—, —$O(CH_2)_3$—, —$(CH_2)_3O$— or —C≡C—;

$S^1$, $S^2$ each independently represent a spacer unit;

R represents a crosslinkable group with the structure $CH_2$=CHCOO—, $CH_2$=C($CH_3$)—COO—, $CH_2$=C(Cl)COO—, $CH_2$=C(Ph)—COO—, $CH_2$=CH—COO—Ph—, $CH_2$=CH—CO—NH—, $CH_2$=C($CH_3$)—CONH—, $CH_2$=C(Cl)—CONH—, $CH_2$=C(Ph)—CONH—, $CH_2$=C(COOR')—$CH_2$—COO—, $CH_2$=CH—OOC—, Ph—CH=CH—, $CH_3$—C(=NR')—, cis or trans-HOOC—R'=CR'—COO—,

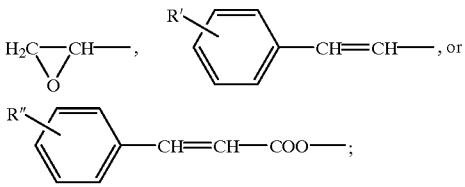

Ph represents phenyl;
R' represents methyl, ethyl, propyl, butyl or pentyl, and
R" represents methyl, methoxy, cyano or halogen,
with the proviso that at least one of the ring systems A or B represents a ring system with the formula $a^1$ or $a^2$, at least one of $Z^1$ and $Z^2$ represent a single bond, and —R—$S^1$ and R—$S^2$ do not contain —O—O or —N—O— groups, wherein the compound is a compound of the formula I-A, I-B, I-C, I-D, I-E, or I-F:

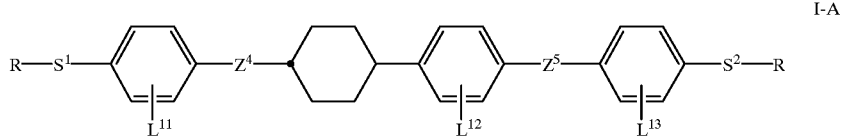

I-A

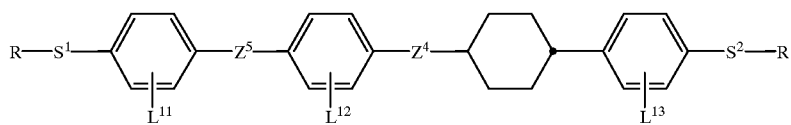

I-B

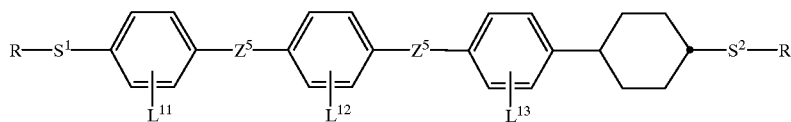

I-C

I-D

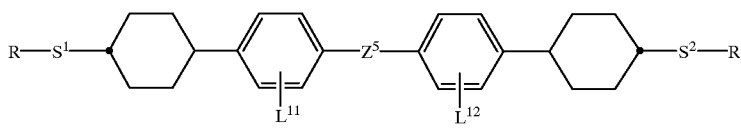

I-E

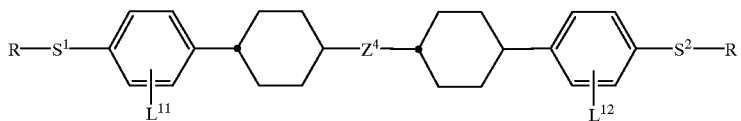

I-F

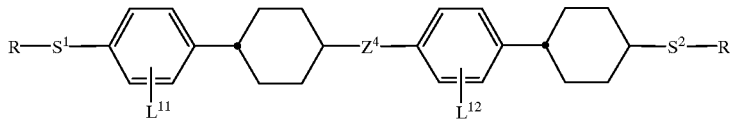

wherein, one or two non-adjacent CH$_2$ groups of the trans-1,4-cyclohexylene ring may be replaced by oxygen and one or two non-adjacent CH groups of the 1,4-phenylene ring may be replaced by nitrogen;

$L^{11}$, $L^{12}$, $L^{13}$ represent, independently, hydrogen, $C_1$–$C_{20}$-alkyl, $C_1$–$C_{20}$-alkenyl, $C_1$–$C_{20}$-alkoxy, $C_1$–$C_{20}$-alkoxycarbonyl, formyl, $C_1$–$C_{20}$-alkylcarbonyl, $C_1$–$C_{20}$-alkylcarbonyloxy, halogen, cyano or nitro;

$Z^4$ represents a single bond, —CH$_2$CH$_2$—, —CH$_2$O—, —OCH$_2$—, —COO—, —OOC—, —(CH$_2$)$_4$—, —O(CH$_2$)$_3$—, —(CH$_2$)$_3$O— or —C≡C—; and $Z^5$ represents a single bond, —CH$_2$CH$_2$—, —CH$_2$O—, —OCH$_2$—, —COO—, —OOC—, or —C≡C—.

3. A compound of the formula I:

R—S$^1$—A—Z$^1$—B—S$^2$—R    I where A and B are each an independent ring system and each have the formula a$^1$, a$^2$ or b, a$^1$

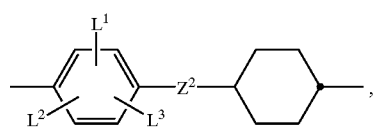

a$^2$

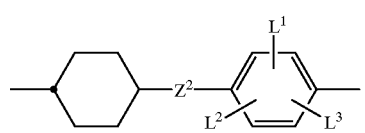

b

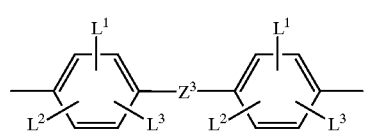

whereby, in the trans-1,4-cyclohexylene ring, one or two non-adjacent CH$_2$ groups may be replaced by oxygen, and whereby, in the 1,4-phenylene ring, one or two non-adjacent CH groups may be replaced by nitrogen;

$L^1$, $L^2$, $L^3$ represent, independently, hydrogen, $C_1$–$C_{20}$-alkyl, $C_1$–$C_{20}$-alkenyl, $C_1$–$C_{20}$-alkyloxy, $C_1$–$C_{20}$-alkyloxy carbonyl, formyl, $C_1$–$C_{20}$-alkyl carbonyl, $C_1$–$C_{20}$-alkyl carbonyloxy, halogen, cyano or nitro;

$Z^1$, $Z^2$, $Z^3$ represent, independently, a single bond, —CH$_2$CH$_2$—, —CH$_2$O—, —OCH$_2$—, —COO—, —OOC—, —(CH$_2$)$_4$—, —O(CH$_2$)$_3$—, —(CH$_2$)$_3$O— or —C≡C—;

$S^1$, $S^2$ each independently represent a spacer unit;

R represents a crosslinkable group with the structure CH$_2$=CHCOO—, CH$_2$=C(CH$_3$)—COO—, CH$_2$=C(Cl)COO—, CH$_2$=C(Ph)—COO—, CH$_2$=CH—COO—Ph—, CH$_2$=CH—CO—NH—, CH$_2$=C(CH$_3$)—CONH—, CH$_2$=C(Cl)—CONH—, CH$_2$=C(Ph)—CONH—, CH$_2$=C(COOR')—CH$_2$—COO—, CH$_2$=CH—OOC—, Ph—CH=CH—, CH$_3$—C(=NR')—, cis or trans-HOOC—R'=CR'—COO—,

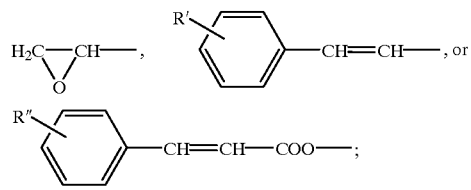

Ph represents phenyl;

R' represents methyl, ethyl, propyl, butyl or pentyl, and

R" represents methyl, methoxy, cyano or halogen, with the proviso that at least one of the ring systems A or B represents a ring system with the formula a$^1$ or a$^2$, at least one of $Z^1$ and $Z^2$ represent a single bond, and —R—S$^1$ and R—S$^2$ do not contain —O—O— or —N—O— groups, wherein the compound is a compound of the formula I-A-1 or I-A-2

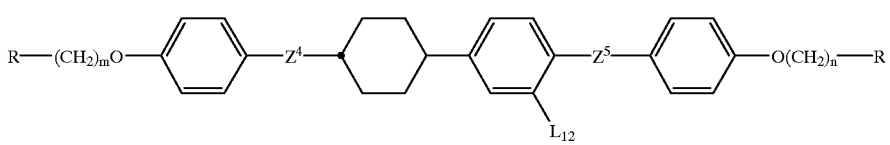

I-A-1

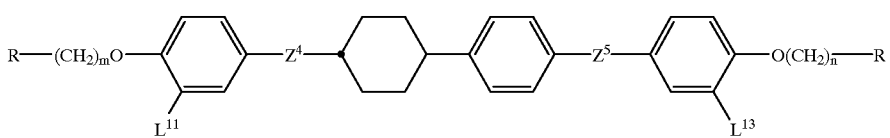

I-A-2 where
- $L^{11}$, $L^{12}$, $L^{13}$ each represent, independently, hydrogen, $C_1-C_{12}$-alkykl, $C_1-C_{12}$-alkenyl, $C_1-C_{12}$-alkoxy, $C_1-C_{12}$-alkoxycarbonyl, formyl, $C_1-C_{12}$-alkylcarbonyl, $C_1-C_{12}$-alkylcarbonyloxy, fluorine, chlorine, cyano or nitro;
- $Z^4$ represents —CH$_2$CH$_2$—, —OCH$_2$, —COO— or —OOC—;
- $Z^5$ represents a single bond, —CH$_2$CH$_2$—, —COO— or —OOC—, or —C≡C—;
- R represents a crosslinkable groups with the structure CH$_2$=CH—, CH$_2$=CHCOO—, CH$_2$=C(CH$_3$)—COO—, CH$_2$=C(Cl)COO—, or

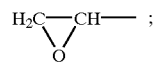

and m, n each represent, indepoendently, a whole number from 2 to 20.

4. A compound according to claim 2 of the formula I-B-1

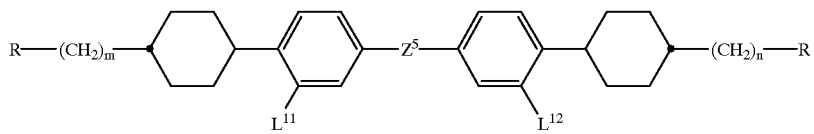

I-B-1 where
- $L^{13}$ represents hydrogen, $C_1-C_{12}$-alkyl, $C_1-C_{12}$-alkenyl, $C_1-C_{12}$-alkoxy, $C_1-C_{12}$-alkoxy-carbonyl, formyl, $C_1-C_{12}$-alkylcarbonyl, $C_1-C_{12}$-alkylcarbonyloxy, fluorine, chlorine, cyano or nitro;
- $Z^4$ represents —CH$_2$—CH$_2$—, —OCH$_2$—, —COO—, or —OOC—;

- $Z^5$ represents a single bond, —CH$_2$CH$_2$—, —COO, —OOC— or —C≡C—;
- R represents a crosslinkable group with the structure CH$_2$=CHCOO—, CH$_2$=C(CH$_3$)—COO—, CH$_2$=C(Cl)COO—, or

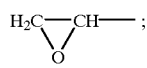

and m, n each represent, independently, a whole number from 2 to 20.

5. A compound according to claim 2 of the formula I-D-1

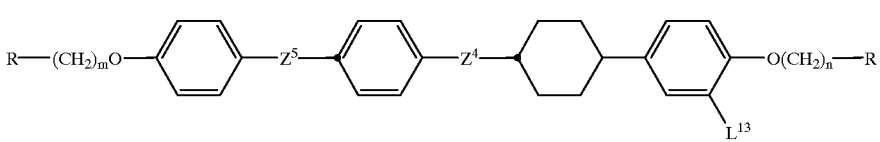

I-D-1 where
- $Z^5$ represents a single bond, —CH$_2$CH$_2$—, —COO, —OOC— or —C≡C—;
- $L^{11}$, $L^{12}$ each represent, independently, hydrogen, $C_1-C_{12}$-alkyl, $C_1-C_{12}$-alkenyl, $C_1-C_{12}$-alkoxy, $C_1-C_{12}$-alkoxycarbonyl, formyl, $C_1-C_{12}$-alkylcarbonyl, $C_1-C_{12}$-alkylcarbonyloxy, fluorine, chlorine, cyano or nitro;
- R represents a crosslinkable group with the structure CH$_2$=CHCOO—, CH$_2$=C(CH$_3$)—COO—, CH$_2$=C(Cl)COO—, or

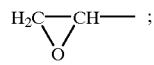

and m, n each represent, independently, a whole number from 2 to 20.

6. A compound of the formula IX

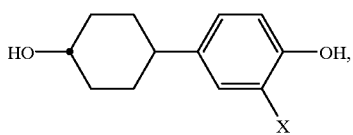  IX where
X represents halogen, —$CH_2$—CH=$CH_2$, —$OR^2$, —$COOR^2$, —$COR^2$, or —$OCOR^2$; and
$R^2$ represents $C_1$–$C_{20}$-alkyl.

7. A crosslinkable liquid crystalline mixture, which comprises at least two components, wherein at least one of the components is a crosslinkable compound according to claim 1.

8. A crosslinkable, liquid crystalline mixture, which comprises at least two components, wherein at least one of the components is a crosslinkable compound of the formula I

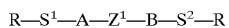  I where
A and B are each an independent ring system and each have the formula $a^1$, $a^2$ or b,

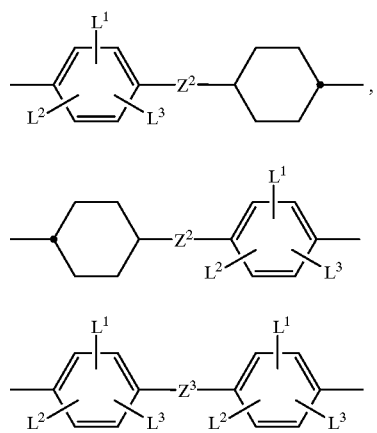

whereby, in the trans-1,4-cyclohexylene ring, one or two non-adjacent $CH_2$ groups may be replaced by oxygen, and whereby, in the 1,4-phenylene ring, one or two non-adjacent CH groups may be replaced by nitrogen;

$L^1$, $L^2$, $L^3$ represent, independently, hydrogen, $C_1$–$C_{20}$-alkyl, $C_1$–$C_{20}$-alkenyl, $C_1$–$C_{20}$-alkyloxy, $C_1$–$C_{20}$-alkyloxy carbonyl, formyl, $C_1$–$C_{20}$-alkyl carbonyl, $C_1$–$C_{20}$-alkyl carbonyloxy, halogen, cyano or nitro;

$Z^1$, $Z^2$, $Z^3$ represent, independently, a single bond, —$CH_2CH_2$—, —$CH_2O$—, —$OCH_2$—, —COO—, —OOC—, —$(CH_2)_4$—, —$O(CH_2)_3$—, —$(CH_2)_3O$— or —C≡C—;

$S^1$, $S^2$ each independently represent a spacer unit;

R represents a crosslinkable group with the structure $CH_2$=CH—, $CH_2$=CHCOO—, $CH_2$=C($CH_3$)—COO—, $CH_2$=C(Cl)COO—, $CH_2$=C(Ph)—COO—, $CH_2$=CH—COO—Ph—, $CH_2$=CH—CO—NH—, $CH_2$=C($CH_3$)—CONH—, $CH_2$=C(Cl)—CONH—, $CH_2$=C(Ph)—CONH—, $CH_2$=C(COOR')—$CH_2$—COO—, $CH_2$=CH—O—, $CH_2$=CH—OOC—, Ph—CH=CH—, $CH_3$—C(=NR')—, cis or trans-HOOC—R'=CR'—COO—,

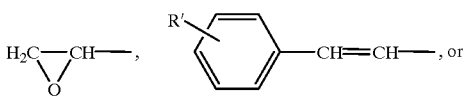

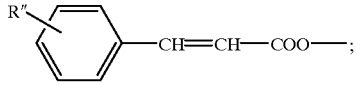

Ph represents phenyl;
R' represents methyl, ethyl, propyl, butyl or pentyl, and
R" represents methyl, methoxy, cyano or halogen, with the proviso that at least one of the ring systems A or B represents a ring system with the formula $a^1$ or $a^2$, at least one of $Z^1$ and $Z^2$ represent a single bond, and —R—$S^1$ and R—$S^2$ do not contain —O—O or —N—O— groups, which also comprises one or more compounds from the group of formulae

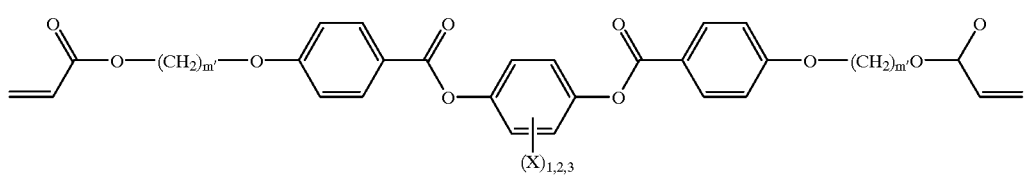  II

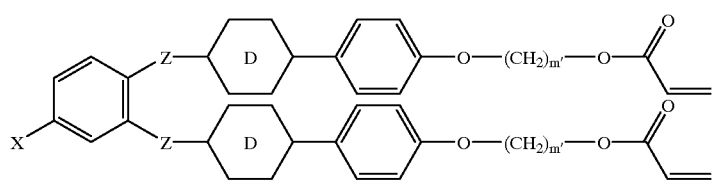  III

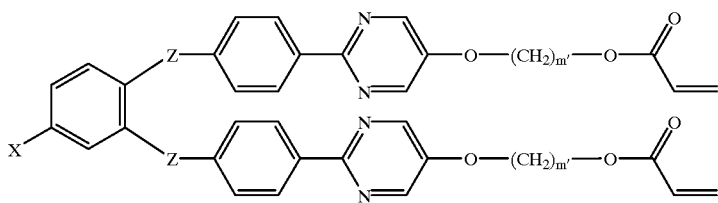

IV

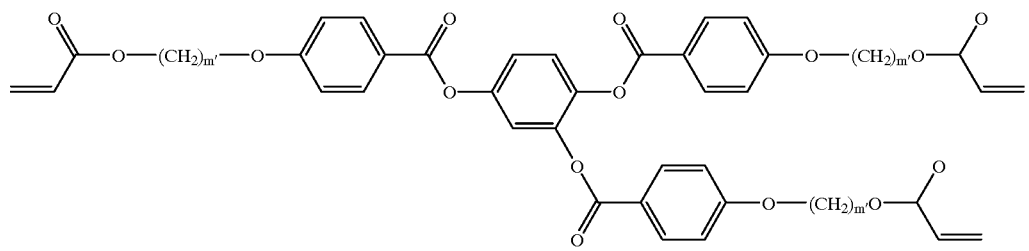

V

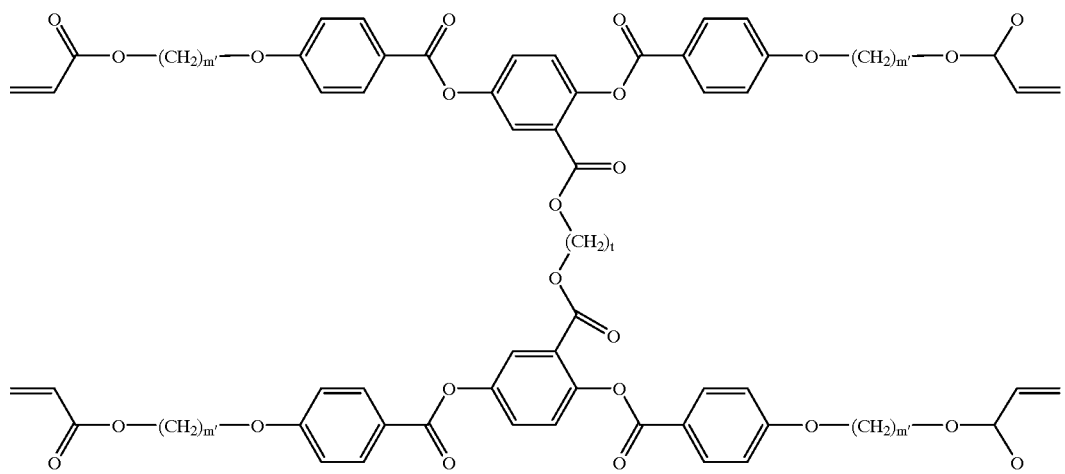

VI

VII 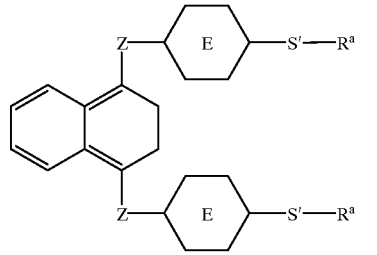

VIII 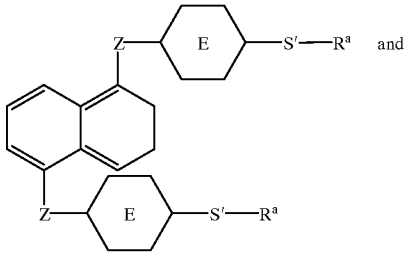  and where

X represents hydrogen, $C_1$–$C_{20}$-alkyl, $C_1$–$C_{20}$-alkenyl, $C_1$–$C_{20}$-alkyoxy, $C_1$–$C_{20}$-alkyoxy carbonyl, formyl, $C_1$–$C_{20}$-alkyl carbonyl, $C_1$–$C_{20}$-alkyl carbonyloxy, halogen, cyan or nitro;

m' represents a whole number from 2 to 20;

t represents a whole number from 2 to 12;

Z represents —COO—, —OOC—, —OCH$_2$—, —CH$_2$O—, —O(CH$_2$)$_3$—, —OOC(CH$_2$)$_2$—, or —COO(CH$_2$)$_3$—;

D represents 1,4-phenylene, trans-1,4-cyclohexylene, pyridine-2,5-diyl, pyrimidine-2,5-diyl or trans-1,4-cyclohexylene-1,4-phenylene;

E represents 1,4-phenylene, or 2- or 3-fluoro-1,4-phenylene;

S' represents —(CH$_2$)$_{m'}$— or —O(CH$_2$)$_{m'}$—;

R$^a$ represents a crosslinkable group with the structure CH$_2$=CH—, CH$_2$=CH—COO—, CH$_2$=C(CH$_3$)—COO—, CH$_2$=C(Cl)—COO—, or

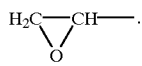

9. An optical component which comprises oriented and crosslinked compounds according to claim 1.

10. An optical component comprising a crosslinkable liquid crystalline mixture according to claim 7.

11. An optical component comprising a crosslinkable liquid crystalline mixture according to claim 8.

12. A compound according to claim 3, wherein R represents a crosslinkable group of the formula $CH_2=CH-COO-$ and m and n each independently represent a whole number from 2 to 12.

13. A compound according to claim 4, wherein $Z^4$ represents $-COO-$, $Z^5$ represents a single bond, and R represents $CH_2=CH-COO-$, and m and n each independently represent a whole number from 2 to 12.

14. A compound according to claim 5, wherein R represents $CH_2=CH-COO-$ and m and n each independently represent a whole number from 2 to 12.

15. A compound according to claim 6, wherein $R^2$ represents $C_1-C_{12}$-alkyl.

16. A method for making a compound of the formula I $$R-S^1-A-Z^1-B-S^2-R \quad\quad I$$

where

A and B are each an independent ring system and each have the formula $a^1$, $a^2$ or b,

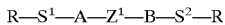

a¹

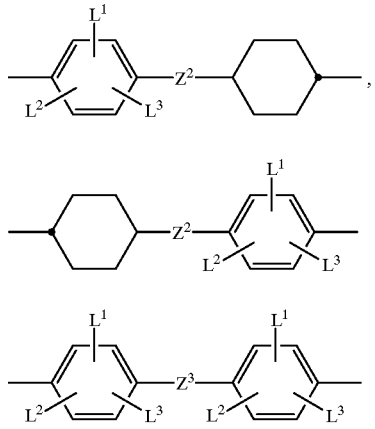

a² b whereby, in the trans-1,4-cyclohexylene ring, one or two non-adjacent $CH_2$ groups may be replaced by oxygen, and whereby, in the 1,4-phenylene ring, one or two non-adjacent CH groups may be replaced by nitrogen;

$L^1$, $L^2$, $L^3$ represent, independently, hydrogen, $C_1-C_{20}$-alkyl, $C_1-C_{20}$-alkenyl, $C_1-C_{20}$-alkyloxy, $C_1-C_{20}$-alkyloxy carbonyl, formyl, $C_1-C_{20}$-alkyl carbonyl, $C_1-C_{20}$-alkyl carbonyloxy, halogen, cyano or nitro;

$Z^1$, $Z^2$, $Z^3$ represent, independently, a single bond, $-CH_2CH_2-$, $-CH_2O-$, $-OCH_2-$, $-COO-$, $-OOC-$, $-(CH_2)_4-$, $-O(CH_2)_3-$, $-(CH_2)_3O-$ or $-C\equiv C-$;

$S^1$, $S^2$ each independently represent a spacer unit;

R represents a crosslinkable group with the structure $CH_2=CH-$, $CH_2=CHCOO-$, $CH_2=C(CH_3)-COO-$, $CH_2=C(Cl)COO-$, $CH_2=C(Ph)-COO-$, $CH_2=CH-COO-Ph-$, $CH_2=CH-CO-NH-$, $CH_2=C(CH_3)-CONH-$, $CH_2=C(Cl)-CONH-$, $CH_2=C(Ph)-CONH-$, $CH_2=C(COOR')-CH_2-COO-$, $CH_2=CH-O-$, $CH_2=CH-OOC-$, $Ph-CH=CH-$, $CH_3-C(=NR')-$, cis or trans-$HOOC-R'CR'-COO-$,

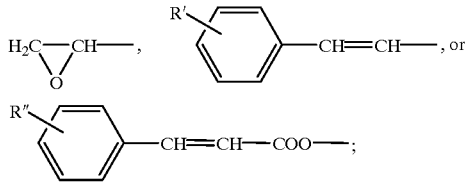

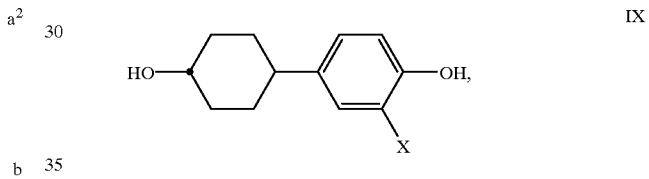

Ph represents phenyl;

R' represents methyl, ethyl, propyl, butyl or pentyl, and

R" represents methyl, methoxy, cyano or halogen, with the proviso that at least one of the ring systems A or B represents a ring system with the formula $a^1$ or $a^2$, at least one of $Z^1$ and $Z^2$ represent a single bond, and $-R-S^1$ and $R-S^2$ do not contain $-O-O$ or $-N-O-$ groups, which comprises reacting a compound of the formula IX,

IX where

X represents halogen, $-CH_2-CH=CH_2$, $-OR^2$, $-COOR^2$, $-COR^2$, or $-OCOR^2$; and $R^2$ represents $C_1-C_{20}$-alkyl;

to obtain the compound of formula I.

17. A crosslinkable liquid crystalline mixture, which comprises at least two components, wherein at least one of the components is a crosslinkable compound according to claim 2.

18. A crosslinkable liquid crystalline mixture, which comprises at least two components, wherein at least one of the components is a crosslinkable compound according to claim 3.

19. An optical component which comprises oriented and crosslinked compounds according to claim 1.

20. An optical component which comprises oriented and crosslinked compounds according to claim 2.

* * * * *

UNITED STATES PATENT AND TRADEMARK OFFICE
CERTIFICATE OF CORRECTION

PATENT NO.  : 6,395,351 B1
DATED       : May 28, 2002
INVENTOR(S) : Benecke et al.

It is certified that error appears in the above-identified patent and that said Letters Patent is hereby corrected as shown below:

<u>Title page,</u>
Item [75], Inventors, "Ohlemacker" should read -- Ohlemacher --

<u>Column 50,</u>
Line 66, "groupwith" should read -- group with --.

<u>Column 51,</u>
Line 30, after "each" (1$^{st}$ occurrence) insert -- an --.

<u>Column 55,</u>
Line 18, "$C_1$-$C_{12}$-alkykl" should read -- $C_1$-$C_{12}$-alkyl --.
Line 27, "groups" should read -- group --.

<u>Column 58,</u>
Lines 53 through 55, formula II, " $\overset{O}{/}$ " should read -- $\overset{O}{\|}$ --.

<u>Column 60,</u>
Lines 12 through 14, formula V, " $\overset{O}{/}$ " should read -- $\overset{O}{\|}$ --.
Lines 17 through 19, formula V, " $\overset{O}{/}$ " should read -- $\overset{O}{\|}$ --.
Lines 22 through 24, formula IV, " $\overset{O}{/}$ " should read -- $\overset{O}{\|}$ --.
Lines 38 through 40, formula VIII, " $\setminus O$ " should read -- $\diagdown\!\!\!\diagup O$ --.

UNITED STATES PATENT AND TRADEMARK OFFICE
CERTIFICATE OF CORRECTION

PATENT NO. : 6,395,351 B1
DATED : May 28, 2002
INVENTOR(S) : Benecke et al.

It is certified that error appears in the above-identified patent and that said Letters Patent is hereby corrected as shown below:

<u>Column 62,</u>
Line 9, "HOOC-R'CR'-COO-" should read -- HOOC-R'=CR'-COO- --.
Line 51, "claim 1" should read -- claim 2 --.
Line 53, "claim 2" should read -- claim 3 --.

Signed and Sealed this

Twentieth Day of August, 2002

Attest:

Attesting Officer

JAMES E. ROGAN
*Director of the United States Patent and Trademark Office*